(12) United States Patent
Sibley et al.

(10) Patent No.: US 12,156,906 B2
(45) Date of Patent: Dec. 3, 2024

(54) IMMUNOLOGICALLY ACTIVE FRAGMENTS OF TOXOPLASMA GONDII

(71) Applicant: Washington University, St. Louis, MO (US)

(72) Inventors: Laurence David Sibley, St. Louis, MO (US); Iti Saraav, St. Louis, MO (US); Qiuling Wang, St. Louis, MO (US); Mary Savari Dhason, St. Louis, MO (US)

(73) Assignee: Washington University, St. Louis, MO (US)

(*) Notice: Subject to any disclaimer, the term of this patent is extended or adjusted under 35 U.S.C. 154(b) by 0 days.

(21) Appl. No.: 17/636,743

(22) PCT Filed: Aug. 19, 2020

(86) PCT No.: PCT/US2020/047048
§ 371 (c)(1),
(2) Date: Feb. 18, 2022

(87) PCT Pub. No.: WO2021/034963
PCT Pub. Date: Feb. 25, 2021

(65) Prior Publication Data
US 2022/0288174 A1 Sep. 15, 2022

Related U.S. Application Data

(60) Provisional application No. 62/888,803, filed on Aug. 19, 2019.

(51) Int. Cl.
*A61K 39/002* (2006.01)
*A61K 39/00* (2006.01)
*A61P 33/02* (2006.01)
*C07K 14/45* (2006.01)
*C07K 16/20* (2006.01)

(52) U.S. Cl.
CPC ............ *A61K 39/002* (2013.01); *A61P 33/02* (2018.01); *C07K 14/45* (2013.01); *C07K 16/20* (2013.01); *A61K 2039/54* (2013.01); *A61K 2039/57* (2013.01)

(58) Field of Classification Search
CPC .............. A61K 39/002; A61K 2039/54; A61K 2039/57; A61P 33/02; C07K 14/45; C07K 16/20
See application file for complete search history.

(56) References Cited

FOREIGN PATENT DOCUMENTS

| WO | 2018085685 | 5/2018 |
| WO | 2021034963 A1 | 2/2021 |

OTHER PUBLICATIONS

PCT/US2020/047048 filed Aug. 19, 2020, International Search Report and Written Opinion dated Jan. 15, 2021.
Reiss, et al., Identification and Characterization of an Escorter for Two Secretory Adhesin in Toxoplasma gondii, The Journal of Cell Biology, vol. 152, No. 3, Feb. 2001, pp. 563-578.
Blumenschein T.M.A., et al., "Atomic Resolution Insight Into Host Cell Recognition by Toxoplasma Gondii," The EMBO Journal, 2007, vol. 26, No. 11, pp. 2808-2820.
Brecht S., et al., "The Toxoplasma Micronemal Protein MIC4 is an Adhesin Composed of Six Conserved Apple Domains," The Journal of Biological Chemistry, Feb. 9, 2001, vol. 276, No. 6, pp. 4119-4127.
Brossier F., et al., "A Spatially Localized Rhomboid Protease Cleaves Cell Surface Adhesins Essential for Invasion by Toxoplasma," Proceedings of the National Academy of Sciences (PNAS), Mar. 15, 2005, vol. 102, No. 11, pp. 4146-4151.
Brown K.M., et al., "Serum Albumin Stimulates Protein Kinase G-Dependent Microneme Secretion in Toxoplasma gondii," The Journal of Biological Chemistry, Apr. 29, 2016, vol. 291, No. 18, pp. 9554-9565.
Diel R., et al., "Comparative Performance of Tuberculin Skin Test, QuantiFERON-TB-Gold in Tube Assay, and T-Spot.TB Test in Contact Investigations for Tuberculosis," Chest, Apr. 2009, vol. 135, No. 4, 14 pages, PMID: 19017873.
Dodangeh S., et al., "A Systematic Review on Efficiency of Microneme Proteins to Induce Protective Immunity Against Toxoplasma gondii," European Journal of Clinical Microbiology & Infectious Diseases, 2019, vol. 38, No. 4, pp. 617-629, PMID: 30680553.
Frenkel J.K., et al., "Dermal Hypersensitivity to Toxoplasma Antigens (Toxoplasmins)," Proceedings of the Society for Experimental Biology and Medicine, May-Jul.-Aug. 1948, vol. 68, pp. 634-639.
Gross S., et al., "Bioluminescence Imaging of Myeloperoxidase Activity in Vivo," Nature Medicine, Apr. 2009, vol. 15, No. 4, pp. 455-461, 15 Pages, DOI:10.1038/nm.1886, XP055425864.
Hoffmann C., et al., "Evolving Characteristics of Toxoplasmosis in Patients Infected With Human Immunodeficiency Virus-1: Clinical Course and Toxoplasma Gondii-specific Immune Responses," Clinical Microbiology and Infectious Diseases, May 2007, vol. 13, No. 5, pp. 510-515.
Howe D.K., et al., "Toxoplasma gondii Comprises Three Clonal Lineages: Correlation of Parasite Genotype with Human Disease," Journal of Infectious Diseases, Dec. 1995, vol. 172, pp. 1561-1566.
Krahenbuhl J.L., et al., "In Vivo and In Vitro Studies of Delayed-Type Hypersensitivity to Toxoplasma gondii in Guinea Pigs," Infection and Immunity, Feb. 1971, vol. 3, No. 2, pp. 260-267, PMID: 16557963; PMC416141.

(Continued)

*Primary Examiner* — Robert A Zeman
(74) *Attorney, Agent, or Firm* — Polsinelli PC

(57) ABSTRACT

*T. gondii* proteins MIC1 and MIC4 are components of excretory/secretory antigens (ESA) that elicit delayed type hypersensitivity (DTH) responses in infected animals. These antigens are capable of inducing IFN-g secretion by splenic T cells (ELISPOT assay), stimulating T cells to produce cytokines that recruit inflammatory monocytes and neutrophils resulting in a positive luminol test (luminol ear assay), and eliciting a positive skin test in the guinea pig.

15 Claims, 3 Drawing Sheets
Specification includes a Sequence Listing.

(56) References Cited

OTHER PUBLICATIONS

Marchant J., et al., "Galactose Recognition by the Apicomplexan Parasite Toxoplasma gondii," The Journal of Biological Chemistry, May 11, 2012, vol. 287, No. 20, pp. 16720-16733, PMID: 22399295; PMC3351351.

Meissner M., et al., "A Family of Transmembrane Microneme Proteins of Toxoplasma gondii Contain EGF-Like Domains and Function as Escorters," Journal of Cell Science, 2002, vol. 115, No. 3, pp. 563-574.

Petruccioli E., et al., "First Characterization of the CD4 and CD8 T-Cell Responses to QuantiFERON-TB Plus," Journal of Infection, 2016, vol. 73, No. 6, pp. 588-597, PMID: 27717779.

Saouros S., et al., "A Novel Galectin-like Domain from Toxoplasma Gondii Micronemal Protein 1 Assists the Folding, Assembly, and Transport of a Cell Adhesion Complex," Journal of Biological Chemistry, Nov. 18, 2005, vol. 280, No. 46, pp. 38583-38591.

Saraav I., et al., "Secretory Microneme Proteins Induce T-Cell Recall Responses in Mice Chronically Infected with Toxoplasma Gondii," mSphere, Jan./Feb. 2019, vol. 4, No. 1, e00711-e00718, 13 pages.

IMMUNOLOGICALLY ACTIVE FRAGMENTS OF TOXOPLASMA GONDII

CROSS REFERENCE TO RELATED APPLICATIONS

This application claims the benefit of International Application No. PCT/US2020/047048, filed Aug. 19, 2020, which claims priority of U.S. Provisional Application No. 62/888,803, filed Aug. 19, 2019, the disclosures of which are is hereby incorporated by reference in their its entirety.

FIELD OF THE TECHNOLOGY

The present disclosure relates to the area of parasite infections. For example, the present disclosure relates to the clinical testing of the parasite *Toxoplasma gondii*. In particular, it relates to cellular immune responses including delayed type hypersensitivity reactions and cytokine release, or interferon gamma secretion assays, and their use in diagnosis of toxoplasmosis.

BACKGROUND

*Toxoplasma gondii* is a parasite that infects as many as one in every four humans. Infections are acquired from eating under cooked meat or ingesting contaminated water. Although toxoplasmosis only rarely causes symptoms, it can become life-threatening if the immune system is weakened by illness or suppressed for organ transplant.

If contracted during pregnancy, toxoplasmosis can cause severe eye and brain damage in the fetus. Pregnant women who are already chronically infected do not pass the parasite to their unborn child as the mothers' own immune response prevents transmission. All of the available medications for treating active toxoplasmosis infections have complications, and there is no cure for the chronic form of the infection.

In *Toxoplasma gondii*, there are three main compartments, called dense granules (GRA proteins), rhoptries (ROP), and micronemes (MIC proteins), which release antigens into the extracellular milieu. Sequential protein secretion from three distinct organelles of *Toxoplasma gondii* accompanies invasion of human fibroblasts. Although both GRA and MIC compartments release antigens constitutively at low levels, micronemes can be stimulated to release large amounts of antigen in response to certain environmental cues, such as contact with host cells or other host factors. Secretion of micronemal proteins is associated with *Toxoplasma* invasion of host cells. Sequential protein secretion from three distinct organelles of *Toxoplasma gondii* accompanies invasion of human fibroblasts. Mobilization of intracellular calcium stimulates microneme discharge in *Toxoplasma gondii*. Collectively, proteins that are released either constitutively or in a regulated fashion have been defined as "excretory secretory antigens (ESA)."

The ESA fraction is enriched in secretory microneme (MIC) proteins but also contains constitutively secreted dense granule (GRA) proteins. Several MIC and GRA proteins have been described. Previous studies have shown that MIC2, and its binding partner MIC2 associated protein (M2AP), are abundant components of ESA. Rapid invasion of host cells by *Toxoplasma* requires secretion of the MIC2-M2AP adhesive protein complex. Molecular characterization of TgMIC5, a proteolytically processed antigen secreted from the micronemes of *Toxoplasma gondii*, have been studied as soluble micronemal proteins that are immunogenic. Several MIC proteins interact: for example MIC1, MIC4 and MIC6 form a complex involved in recognition of host carbohydrates. Gene deletions of MIC1 or MIC3 alone do not have a profound effect on invasion, but the double mutant is attenuated, indicating these proteins plan complementary roles. MIC1 has been used in a variety of immunodiagnostic assays based on detection of antibodies that react to this protein or to hybrid proteins containing MIC1 and other parasite antigens. As well, MIC1 and MIC4 have been used in vaccination studies in mice. Other studies have shown that the secretory proteins GRA4, GRA6, and GRA7 are targets of the immune response.

Delayed type hypersensitivity (DTH) responses are driven by cellular immune responses to antigens. Typically a test antigen is injected in the skin of the ear, flank, or footpad and swelling measured 24-48 hr later. The most well-known test uses tuberculin, an extract of purified protein derivative (PPD) from mycobacteria, which is used in a skin test for tuberculosis infection. The skin test is also the basis for many allergy testing protocols. Although previous studies have used skin testing of toxoplasmin in mice and hamsters based on swelling and redness, these assays have not proven to be that specific or sensitive. Previous studies testing toxoplasmin, a skin test reaction elicited by ESA antigens, showed that it was sensitive and specific for detecting individuals in France that were chronically infected with *T. gondii*. In those studies, the ES antigen was made from culture supernatants, fixed with formalin, and then dialyzed with a 10 kDa filtration step. In subsequent studies, others have indicated that the active component in toxoplasmin is in the range of 10 kDa to 50 kDa based on filtration. Approximative molecular weight of the active component in toxoplasmin. It should be noted that proteins may undergo proteolytic processing or breakdown, so this size range does not necessarily indicate the size or identity of the full-length protein. Although these studies refined the knowledge of the active components of ESA, the active components remain undefined at the molecular level. Moreover, there is no way to produce the ESA fraction in large quantities such that it could be made into a commercial product. Delayed type hypersensitivity reactions are predominately driven by CD4+ memory T cells that recognize antigen from a previous exposure. Upon recognition of their cognate antigen, these memory T cells expand and produce cytokines including interferon gamma (IFN-γ) tumor necrosis factor (TNF) and other chemokines. This initial reaction also results in recruitment of mononuclear (i.e. monocytes) cells and polymorphonuclear (i.e. PMNs) cells from circulation into the tissue. Although the conventional DTH test relies on monitoring induration, and redness that develop at the site of injection, more recent tests have been developed to directly monitor T cells responses to specific antigens. Typically these responses are monitored in circulating T cells obtained from the leukocyte fraction of whole blood. Leukocytes, including antigen-presenting cells and T cells, are mixed in vitro with antigens and the resulting responses monitored by production of IFN-γ or other cytokines. In some applications there are referred to as INFγ-release or IFN-γ-secretion assays, owing the fact that IFN-γ is the primary cytokine thought to drive the DTH response. The advantages of such tests is that they are more quantitative than the traditional skin test, they can be completed with a single office visit, and they often suffer less from cross-reaction to environmental antigens.

The enzyme-linked immunospot or ELISpot assay was originally developed for detecting B cells that were secreting antigen-specific antibodies a solid-phase immunoenzymatic technique for the enumeration of specific antibody-secreting cells. It has since been modified to detect cytokines secreted by different immune cells. The principle of the assay is that it relies on a sandwich ELISA where a membrane-backed microplate (typically polyvinylidene difluoride) is coated with antibodies to a particular cytokine. Cells from healthy or immune donors are added the plate and incubated overnight in medium under standard culture conditions. Cytokines secreted during this incubation are captured by the antibody-coated membrane. Following the incubation period, the cells are washed off and the captured cytokine is detected by a second antibody that is specific for the protein of interest. Detection is accomplished using an enzyme-linked reagent, either secondary antibody, or streptavidin to detect the biotinylated primary antibody.

ELISpot assays have previously been used for detection of IFN-γ secretion by T cells in patients that were chronically infected with *Toxoplasma gondii*. This study focused on immunocompromised patients and used the ELISpot assay as a surrogate for CD4+ T cell responses to whole antigen. Although this study did not evaluate the ELISpot assay as a primary diagnostic tool, it suggests that the degree of immunity in a patient can be inferred from the strength of the response in the ELISpot assay. In this case the ELISpot test was conducted with whole parasite antigen and no attempt was made to define useful antigens that would increase sensitivity or specificity using this assay.

Toxoplasmosis is typically diagnosed by a blood test. There is a continuing need in the art to develop a more convenient skin test to detect chronic infection. This test would potentially be faster, more effective, less expensive and therefore would be invaluable for pregnant women, those awaiting organ transplant, or those suffering from illnesses that weaken the immune system.

SUMMARY

According to one aspect of the disclosure, a *Toxoplasma gondii* excretory secretory antigen is provided antigen composition is provided. The composition comprises a *Toxoplasma gondii* excretory secretory antigen selected from the group consisting of: isolated and purified amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), MIC4 C-Terminal amino acids (SEQ ID NO: 8), MIC4 MID domain amino acids (SEQ ID NO: 14) and combinations thereof as elements of an antigen or components of a composition. In some embodiments, the *Toxoplasma gondii* excretory secretory antigen is devoid of contamination with lipopolysaccharide, having less than 0.1 EU/ml of lipopolysaccharide; a genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen and combinations thereof as elements of an antigen or components of a composition.

Another aspect of the invention is a nucleic acid which encodes a purified protein fragment of a *Toxoplasma gondii* excretory secretory antigen. The nucleic acid sequence may encode a purified protein fragment comprises amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), MIC4 C-Terminal amino acids (SEQ ID NO: 8), or MIC4 MID domain amino acids (SEQ ID NO: 14). Additionally, the nucleic acid sequence may encode an antigenic peptide with less than ½ the molecular weight of its corresponding full length protein MIC1 or MIC4; devoid of at least N-terminal amino acid residues 1-19 of its corresponding full length protein MIC1 (SEQ ID NO: 1) or MIC4 (SEQ ID NO: 4); devoid of at least N-terminal amino acid residues 1-100 of MIC1 as determined by sequence alignment with SEQ ID NO: 1 or MIC4 as determined by sequence alignment with SEQ ID NO: 4; genetically encoded as a fusion protein; or covalently attached to a moiety that enhances or facilitates purification, recombinant production, or immune cell stimulation. In some embodiments, the nucleic acid comprises a sequence selected from 10, 11, 12, 13, 15 and 16. In each of the above described embodiments, the nucleic acid is codon-optimized for expression in a non-*Toxoplasma* host cell.

According to yet another aspect of the disclosure is provided a method of delivering *Toxoplasma gondii* excretory secretory antigen to a subject is provided. The method generally comprises an applicator device that is loaded with a *Toxoplasma gondii* excretory secretory antigen composition according to the disclosure and is contacted with skin of the subject. The *Toxoplasma gondii* excretory secretory antigen composition is thereby delivered to the skin of the subject. The composition comprises a *Toxoplasma gondii* excretory secretory antigen selected from the group consisting of: isolated and purified amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), MIC4 C-Terminal amino acids (SEQ ID NO: 8), MIC4 MID domain amino acids (SEQ ID NO: 14), and combinations thereof as elements of an antigen or components of a composition. In some embodiments, the *Toxoplasma gondii* excretory secretory antigen is devoid of contamination with lipopolysaccharide, having less than 0.1 EU/ml of lipopolysaccharide; a genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen and combinations thereof as elements of an antigen or components of a composition.

An additional aspect of the invention is a method of testing a mammal for infection by *T. gondii*. A purified protein fragment is administered under the skin of the mammal. The purified protein fragment comprises a portion of a *Toxoplasma gondii* excretory secretory antigen. It comprises amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), MIC4 C-Terminal amino acids (SEQ ID NO: 8), or MIC4 MID domain amino acids (SEQ ID NO: 14). The protein fragment is: devoid of at least N-terminal amino acids 1-19 of its corresponding full length protein MIC1 (SEQ ID NO: 1) or MIC4 (SEQ ID NO: 4); substantially lacks contamination with lipopolysaccharide, having less than 0.1 EU/ml of lipopolysaccharide; genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen.

Yet another aspect of the disclosure is a method of eliciting and/or monitoring a T cell response in a subject. A *Toxoplasma gondii* excretory secretory antigen composition is contacted with T cells of the subject. The *Toxoplasma gondii* excretory secretory antigen composition induces a T cell response, which may involve production or secretion of cytokines. The *Toxoplasma gondii* excretory secretory antigen composition is selected from the group consisting of: isolated and purified amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), MIC4 C-Terminal amino acids (SEQ ID NO: 8), MIC4 MID domain amino acids (SEQ ID NO: 14), and combinations thereof as elements of an antigen or components of a composition. In some embodiments, the *Toxoplasma gondii* excretory secretory antigen is devoid of contamination with lipopolysaccharide, having less than 0.1 EU/ml of lipopolysaccharide; a genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen and combinations thereof as elements of an antigen or components of a composition.

Still another aspect of the disclosure is a method of delivering a purified protein fragment of a *Toxoplasma gondii* excretory secretory antigen to a subject. An applicator device which is loaded with a purified protein fragment of a *Toxoplasma gondii* excretory secretory antigen is contacted with skin of the subject. The purified protein fragment of a *Toxoplasma gondii* excretory secretory antigen is thereby delivered to the skin of the subject. The purified protein fragment comprises amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), MIC4 C-Terminal amino acids (SEQ ID NO: 8), or MIC4 MID domain amino acids (SEQ ID NO: 14). The protein fragment is: devoid of at least N-terminal amino acids 1-19 of its corresponding full length protein MIC1 (SEQ ID NO: 1) or MIC4 (SEQ ID NO: 4); devoid of contamination with lipopolysaccharide, having less than 0.1 EU/ml of lipopolysaccharide; genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen.

In one aspect of the disclosure provides a method of treating or preventing a *Toxoplasma gondii* infection in a subject in need thereof, the method comprising administering to the subject an effective amount of a compostions comprising a *Toxoplasma gondii* excretory secretory antigen as described herein.

Yet another aspect of the disclosure is an applicator device for administering a purified protein fragment of a *Toxoplasma gondii* excretory secretory antigen to a mammal. The purified protein fragment comprises amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), MIC4 C-Terminal amino acids (SEQ ID NO: 8), or MIC4 MID domain amino acids (SEQ ID NO: 14).

Another aspect of the invention is a kit that comprises (a) a purified protein fragment of a *Toxoplasma gondii* excretory secretory antigen and (b) an applicator device for administration of the *Toxoplasma gondii* excretory secretory antigen to a subject. The purified protein fragment comprises amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), or MIC4 C-Terminal amino acids (SEQ ID NO: 8), MIC4 MID domain amino acids (SEQ ID NO: 14). The protein fragment is: devoid of at least N-terminal amino acids 1-19 of its corresponding full length protein MIC1 MGQALFLTVLLPVLFGVGPEAYGEASHSHSPAS-GRYIQQMLDQRCQEIAAELCQGGL RKMCVPSSRI-VARNAVGITHQNTLEWRCFDTASLLESNQENNGV NCVDDCGHTIPCP GGVHRQNSNHATRHEILSK-LVEEGVQRFCSPYQASANKYCNDKFPGTIARR-SKGFG NNVEVAWRCYEKASLLYSVYAECASNC GTTWYCPGGRRGTSTELDKRHYTEEEGIR QAIGSV DSPCSEVEVCLPKDENPPVCLDESGQISRTGGGPP-SQPPEMQQPADRSDE RGGGKEQSPGGEAQPDHP TKGGNIDLPEKSTSPEKTPKTEIHGDSTKATLEEGQ QLT LTFISTKLDVAVGSCHSLVANFLDGFLKFQTGSN-SAFDVVEVEEPAGPAVLTIGLGHK GRLAVVLDYTRL-NAALGSAAYVVEDSGCSSSEEVSFQGVGSGATLVVT-TLGESPTAV SA (SEQ ID NO: 1) or MIC4 MRASLPVHLWCTQLSAVWFGVAKAHGGHRLEPHV PGFLQGFTDITPAGDDVSANV TSSEPAKLDLSCVHS DNKGSRAPTIGEPVPDVSLEQCAAQCKAVDGCTH FTYNDDSK MCHVKEGKPDLYDLTGGKTASRSCDR SCFEQHVSYEGAPDVMTAMVTSQSADCQA ACAA DPSCEIFTYNEHDQKCTFKGRGFSAFKERGVLGVT SGPKQFCDEGGKLTQEE MEDQISGCIQLSDVGSMTA-DLEEPMEADSVGACMERCRCDGRCTHFTFNDN-TRMC YLKGDKMQLYSSPGDRTGPKSCDSSCFSNG VSYVDDPATDVETVFEISHPIYCQVIC AANPLCTVF QWYASEAKCWKRKGFYKHRKTGVTGVTVGPREFC DFGGSIRDREEA DAVGSDDGLNAEATMANSPDFH DEVECVHTGNIGSKAQTIGEVKRASSLSECRARC QA EKECSHYTYNVKSGLCYPKRGKPQFYKYLGDMT GSRTCDTSCLRRGVDYSQGP EVGKPWYSTLPTDCQ-VACDAEDACLVFTWDSATSRCYLIGSGFSAHRRND VDGVVS GPYTFCDNGENLQVLEAKDTE (SEQ ID NO: 4); devoid of contamination with lipopolysaccharide, having less than 0.1 EU/ml of lipopolysaccharide; genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen.

These and other embodiments, which will be apparent to those of skill in the art upon reading the specification, provide the art with tools for identifying *T. gondii* infections in individuals and in populations.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION

Figure 1:
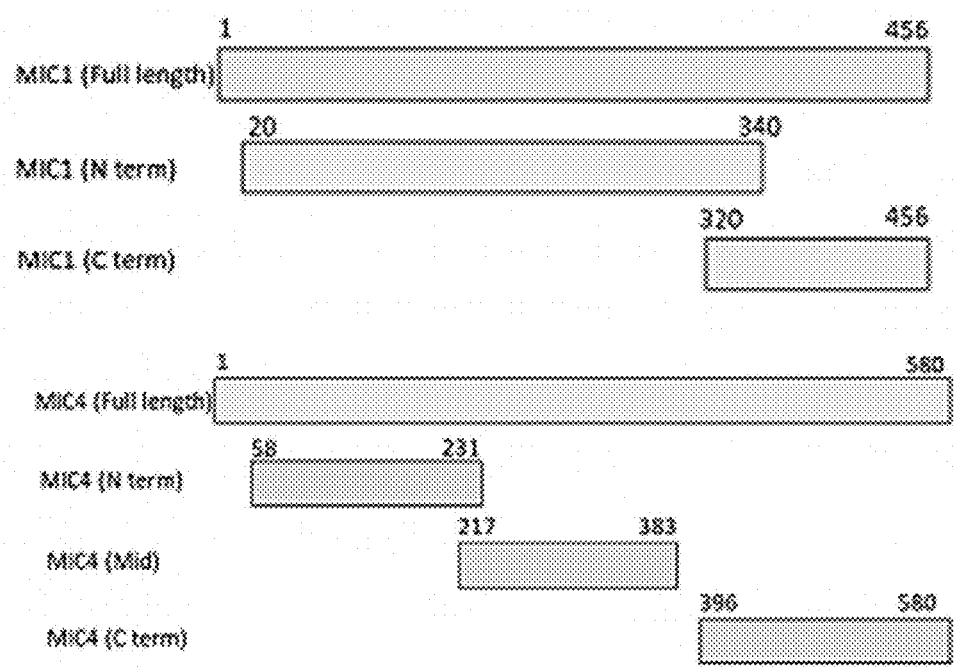
FIG. 1 depicts diagrams of amino acid positions of MIC1 and MIC4 constructs.

The present disclosure provides, in part, a standardized, abundant test antigen composition for use in sensitively and specifically testing individuals for infection by *Toxoplasma gondii*. Antigens that cause a non-specific reaction (whether the subject has been infected or not) and antigens that cause a specific reaction (only in subject that has been infected) have been identified. The latter have been purified and cloned and modified to form test reagents. The former have been eliminated from test reagents. In particular, *T. gondii* antigens MIC1 and MIC4 have been cloned and expressed in *E. coli* which include pieces of the peptides that were missing from prior constructs. The recombinant protein fragments have also been purified. These new constructs, including the C terminal (C term) portion of MIC1 and the middle (Mid) portion of MIC4 gave positive results in the ELISPOT assay, which measures release of interferon gamma. New constructs MIC1 (C term) and MIC4 (Mid) also gave positive results in the ear luminol assay in mouse and in the skin test in guinea pig, confirming that they elicit a DTH response.

MIC1 is normally a 456 residue (amino acid) protein that is processed in the parasite remove the N-terminal 16 residues. This leaves a total size of 440 residues. In contrast to this native protein, in some embodiments, the purified protein fragment disclosed herein comprises amino acid residues 20-340 of MIC1 EAYGEASHSHSPAS-GRYIQQMLDQRCQEIAAELCQGGLRKMCVPSSRI-VARNAVGIT HQNTLEWRCFDTASLLESNQENNG VNCVDDCGHTIPCPGGVHRQNSNHATRHEILS KLV EEGVQRFCSPYQASANKYCNDKFPGTIARRSKGF GNNVEVAWRCYEKASLLYS VYAECASNCGTTWY CPGGRRGTSTELDKRHYTEEEGIRQAIGSVDSPC-SEVEVCLP KDENPPVCLDESGQISRTGGGPPSQPPE MQQPADRSDERGGGKEQSPGGEAQPD HPTKGG-NIDLPEKSTSPEKTPK (SEQ ID NO: 2), or amino acid residues 320-456 of MIC1 KTEIHGDSTKATLEEG QQLTLTFISTKLDVAVGSCHSLVANFLDGFLKFQTG-SNSAFD VVEVEEPAGPAVLTIGLGHKGRLAVVLDYT RLNAALGSAAYVVEDSGCSSSEEVSFQ GVGS-GATLVVTTLGESPTAVSA (SEQ ID NO: 3).

In an embodiment, purified protein fragment of the composition is a sequence comprising at least 80% identity to SEQ ID NO:2. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:2.

In an embodiment, purified protein fragment of the composition is a sequence comprising at least 80% identity to SEQ ID NO:3. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:3.

MIC4 is normally a 580 residue (amino acid) protein that is processed in the parasite to remove the N-terminal 25 amino acids. This leaves a mature protein of 555 amino acids. In some embodiments, the purified MIC4 protein fragment as disclosed herein comprises amino acid residues 58-231 of MIC4 SSEPAKLDLSCVHSDNKGSRAP-TIGEPVPDVSLEQCAAQCKAVDGCTHFTYNDDS KMCHVKEGKPDLYDLTGGKTASRSCDRSCFEQH VSYEGAPDVMTAMVTSQSADC QAACAADPSCEIFT YNEHDQKCTFKGRGFSAFKERGVLGVTSGPKQFC-DEGGKLT QEEMEDQISG (SEQ ID NO: 5), amino acid residues 217-383 of MIC4 GGKLTQEEMEDQISGCI-QLSDVGSMTADLEEPMEADSVGACMERCRCDG RCTHF TFNDNTRMCYLKGDKMQLYSSPGDRTG PKSCDSSCFSNGVSYVDDPATDVETVF EISHPIYCQ VICAANPLCTVFQWYASEAKCVVKRKGFYKHR KTGVTGVTVGPREFC DFG (SEQ ID NO: 6), amino acid residues 396-580 of MIC4 GSDDGLNAEAT-MANSPDFHDEVECVHTGNIGSKAQTIGEVKRAS SLSECRARCQA EKECSHYTYNVKSGLCYPKRGKP QFYKYLGDMTGSRTCDTSCLRRGVDYSQGPE VGK PWYSTLPTDCQVACDAEDACLVFTWDSATSRCY LIGSGFSAHRRNDVDGVV SGPYTFCDNGENLQVLE AKDTE (SEQ ID NO: 7), amino acids of the MIC4 C-TERM SDDGLNAEATMANSPDFHDEVECVHTG NIGSKAQTIGEVKRASSLSECRARCQAE KECSHY-TYNVKSGLCYPKRGKPQFYKYLGDMTGSRTCDTSC LRRGVDYSQGPEV GKPWYSTLPTDCQVACDAEDA-CLVFTWDSATSRCYLIGSGFSAHRRNDVDGVVS GPY-TFCDNGENLQVLEAKDTE (SEQ ID NO: 8), or amino acids residues of MIC4 MID GKLTQEEMEDQISGCI-QLSDVGSMTADLEEPMEADSVGACMERCRCDGR CTHFT FNDNTRMCYLKGDKMQLYSSPGDRTGP KSCDSSCFSNGVSYVDDPATDVETVFEI SHPIYCQVI-CAANPLCTVFQWYASEAKCVVKRKGFYKHRKT GVTGVTVGPREFCD FG (SEQ ID NO: 14).

In an embodiment, purified protein fragment of the composition is a sequence comprising at least 80% identity to SEQ ID NO:5. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:5.

In an embodiment, purified protein fragment of the composition is a sequence comprising at least 80% identity to SEQ ID NO:6. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:6.

In an embodiment, purified protein fragment of the composition is a sequence comprising at least 80% identity to SEQ ID NO:7. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:7.

In an embodiment, purified protein fragment of the composition is a sequence comprising at least 80% identity to SEQ ID NO:8. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:8.

In an embodiment, purified protein fragment of the composition is a sequence comprising at least 80% identity to SEQ ID NO:14. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:14.

In some embodiments, the antigenic peptides disclosed herein are covalently attached to a moiety that enhances or facilitates purification, recombinant production, or immune cell stimulation. Thus, an antigenic peptide comprises at least one purification tag. The purification tag may be any known in the art, in non-limiting examples, a FLAG tag and a His tag. The disclosure also encompasses a nucleic acid molecule encoding an antigenic peptide as described herein. Additionally, the disclosure encompasses a pharmaceutical composition comprising an antigenic peptide as described herein.

The compositions of antigens preferably contain only antigens that cause a specific reaction and are devoid of antigens that cause a non-specific reaction. Such preparation may be made by any means known in the art, including isolation and purification from, e.g., natural sources, recombinant production, or synthetic production. Carriers for the antigens may be any standardly used, typically a carrier that does not itself cause a DTH reaction or inhibit a DTH reaction by a bona fide antigen. Non-limiting examples of excipients that may be used for the antigen compositions are sucrose, mannitol, trehalose, and Hemaccel™ (intravenous colloid). Buffers, salts, sugars, preservatives, isotonic saline solutions, phosphate-buffered saline, can also be used in the compositions. Additional components and excipients include water, polymers, fatty acid esters, parabens. Compositions may be stored as convenient, including without limitation as lyophilized samples, at about or below 4° C., and at about or below −70° C.

In some embodiments, N-terminal portions of the proteins that are not present in the antigenic protein fragments. In non-limiting examples, the antigenic fragments may be devoid of amino acids 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, -192, 1-93, 1-94, 1-95, 1-96, 1-97, 1-98, 1-99, or 1-100, as determined by sequence alignment with SEQ ID NO:1 or SEQ ID NO:4. In some aspects, these N-terminal sequences may not be necessary for achieving good immune reactions in the ELISPOT, ear luminol, or skin DTH tests.

In some embodiments, excellent function in immune reaction assessments may be retained in the protein fragments when only a fraction of the protein is used. In non-limiting examples, the fragments may be less than 90%, less than 80%, less than 70%, less than 60%, less than 50%, less than 40%, or less than 30% of the amino acid residues of the full length protein to which it corresponds, SEQ ID NO:1 or SEQ ID NO:4.

The antigenic protein fragments produced in recombinant bacterial may undesirably contain lipopolysaccharide (LPS). The protein fragments can be purified to minimize contamination with LPS. Levels of LPS may be reduced to less than 0.5 EU/ml, less than 0.25 EU/ml, less than 0.1 EU/ml, and less than 0.05 EU/ml. Other undesirable contaminants may also be removed.

Compositions of antigens may be free of other ESA components such as dense granular proteins (GRA), other microneme proteins, or other components which lead to lower sensitivity and/or specificity. An isolated and purified preparation may be from *T. gondii* organisms, from a recombinant host cell, or from a synthetic in vitro reaction. The isolated and purified protein may comprise at least 1%, at least 5%, at least 10%, at least 20%, at least 25%, at least 30%, at least 40%, at least 50%, at least 60%, at least 70%, at least 75%), at least 80%, at least 85%, at least 90%, at least 95%, at least 97%, or at least 99% of the protein in a composition.

Testing for DTH may be used in order to prevent or detect congenital toxoplasmosis, for example by testing women before or during pregnancy, respectively. Primary infection of pregnant women may lead to abortion or severe neonatal malformation. Testing may also be used in immunocompromised patients, in whom a severe form of the disease may be fatal. Testing for DTH might also be performed in healthy adults to determine their infectious status prior to performing a medical procedure as a consequence of which they may become immunocompromised. Detection of infection may be critical in managing the disease. If a positive DTH test occurs, it may be desirable to follow it with a serum test. Because the two types of tests detect different immunological pathways and components, the two types of tests may give complementary information. Serum tests detect antibodies, whereas DTH tests detect cellular immune responses.

As an alternative, an in vitro reaction may be used to detect a T cell response. The in vitro reaction may be performed on any source of T cells, including whole blood, serum, plasma, and other tissue sources of T cells. The T cells are contacted with one or more of the *Toxoplasma gondii*-antigens or an antigen composition. If the T cells are reactive with the antigens or antigen composition they release a cytokine such as interferon-γ or other cytokines. The presence of interferon-γ or other released cytokine can be detected using any technique known in the art, including but not limited to an antibody or a series of antibodies. The antibodies may be labeled for detection. An antibody may be attached to an enzyme, such as horseradish peroxidase or alkaline phosphatase that produces colored products in the presence of appropriate substrates. An antibody may be fluorescently labeled, as an alternative. The in vitro reaction product may be captured on a solid support or assayed in the reaction fluid.

Kits may comprise an outer package to contain all components as well as optional inner packaging to contain individual components or combinations of components. Optional components include instructions for assembly and/or administration, information on side effects, expiry information, etc. Information may be provided in paper form, on a digital medium, or as an internet address to such information.

Applicators may be any type as is known in the art for administering an antigen to the skin of a subject and developing a DTH response. These include without limitation patches, needles, multi-needle assemblies, prongs, multi-prong assemblies. Antigens may be administered individually at separate locations or in combination at a single location.

Fusion proteins can be made using recombinant DNA technology to express two or more proteins or polypeptide portions of proteins as a single expression product. Any suitable technique known in the art for making and expressing such fusion proteins may be used. In some embodiments, a non-*T. gondii* protein is fused to a *T. gondii* protein. In other embodiments, two distinct *T. gondii* proteins are fused together.

Amounts of antigen composition that may be administered can be empirically determined, but may be between 0.1 and 50 ug, between 0.5 and 25 ug, or between 1 and 10 ug.

Suitable subjects include, but are not limited to, a human, a livestock animal, a companion animal, a lab animal, and a zoological animal. A subject may or may not be known to have a *T. gondii*-mediated disorder. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the animal is a laboratory animal. Non-limiting examples of a laboratory animal may include rodents, canines, felines, and non-human primates. In another preferred embodiment, the subject is a human.

Previous studies have identified short peptide residues that enhance uptake by dendritic cells and increase the efficiency of antigen presentation [Sioud, M., et al., A novel peptide carrier for efficient targeting of antigens and nucleic acids to dendritic cells. FASEB J, 2013. 27(8): p. 3272-83]. The receptor to which these peptides bind on host dendritic cells is not known. Nonetheless, it is likely that these short sequences work by enhancing uptake of the antigen and priming the presentation pathway. These steps of antigen uptake, processing, and presentation are critical for the DTH response. MIC1, MIC4 and truncated and/or fused forms of these proteins, can be expressed so that these sequences are either at the N- or C-termini. These modified antigens can be purified under conditions that minimize contamination with LPS. Levels of LPS may be reduced to less than 0.5 EU/ml, less than 0.25 EU/ml, less than 0.1 EU/ml, and less than 0.05 EU/ml.

The present disclosure also provides pharmaceutical compositions. The pharmaceutical composition comprises a composition of the invention which is detailed above, as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palm itate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980).

The above disclosure generally describes the present invention. All references disclosed herein are expressly incorporated by reference. A more complete understanding can be obtained by reference to the following specific examples that are provided herein for purposes of illustration only, and are not intended to limit the scope of the invention.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a peptide of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of the invention may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palm itate), n-octadecanoate (stearate), n-eicosanoate (arachidate), n-docosanoate (behenate), n-tetracosanoate (lignocerate), cis-9-hexadecenoate (palm itoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the compound of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm In certain aspects, a pharmacologically effective amount of a composition of the invention may be administered to a subject. Administration is performed using standard effective techniques. Peripheral administration includes but is not limited to intravenous, intraperitoneal, subcutaneous, and pulmonary, transdermal, intramuscular, intranasal, buccal, sublingual, or suppository administration.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hem isuccinate, phosphatidyl glycerols and the like.

For therapeutic applications, a therapeutically effective amount of a composition of the invention is administered to a subject. A "therapeutically effective amount" is an amount of the therapeutic composition sufficient to produce a measurable response (e.g., an immunostimulatory). Actual dosage levels of active ingredients in a therapeutic composition of the invention can be varied so as to administer an amount of the active compound(s) that is effective to achieve the desired response for a particular subject. The selected dosage level will depend upon a variety of factors including the activity of the therapeutic composition, formulation, the route of administration, combination with other drugs or treatments, and the physical condition and prior medical history of the subject being treated.

The frequency of dosing may be once, twice, three times or more daily or once, twice, three times or more per week or per month, as needed as to effectively treat the symptoms or disease. In certain embodiments, the frequency of dosing may be once, twice or three times daily. For example, a dose may be administered every 24 hours, every 12 hours, or every 8 hours. In a specific embodiment, the frequency of dosing may be twice daily.

Duration of treatment could range from a single dose administered on a one-time basis to a life-long course of therapeutic treatments. The duration of treatment can and will vary depending on the subject and the cancer or autoimmune disease or infection to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, or 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The timing of administration of the treatment relative to the disease itself and duration of treatment will be determined by the circumstances surrounding the case. Treatment could begin immediately, such as at the time of diagnosis, or treatment could begin following surgery. Treatment could begin in a hospital or clinic itself, or at a later time after discharge from the hospital or after being seen in an outpatient clinic.

Although the foregoing methods appear the most convenient and most appropriate and effective for administration of a composition of the invention, by suitable adaptation, other effective techniques for administration, such as intraventricular administration, transdermal administration and oral administration may be employed provided proper formulation is utilized herein.

Another aspect of the disclosure is provided a method of delivering *Toxoplasma gondii* excretory secretory antigen to a subject is provided. The method generally comprises administering the *Toxoplasma gondii* excretory secretory antigen to a subject with an applicator device that is loaded with a *Toxoplasma gondii* excretory secretory antigen composition according to the disclosure and is contacted with skin of the subject. The *Toxoplasma gondii* excretory secretory antigen composition is thereby delivered to the skin of the subject. The composition comprises a *Toxoplasma gondii* excretory secretory antigen selected from the group consisting of: isolated and purified amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), and combinations thereof as elements of an antigen or components of a composition. In some embodiments, the *Toxoplasma gondii* excretory secretory antigen is devoid of contamination with lipopolysaccharide, having less than 0.1 EU/ml of lipopolysaccharide; a genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen and combinations thereof as elements of an antigen or components of a composition.

An additional aspect of the invention is a method of testing a mammal for infection by *T. gondii*. The method generally comprises administering to a subject in need thereof a purified protein fragment under the skin. The purified protein fragment comprises a portion of a *Toxoplasma gondii* excretory secretory antigen. It comprises amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), or amino acid residues 396-580 of MIC4 (SEQ ID NO: 7). The protein fragment is: devoid of at least N-terminal amino acids 1-19 of its corresponding full length protein MIC1 (SEQ ID NO: 1) or MIC4 (SEQ ID NO: 4); substantially free of contamination with lipopolysaccharide, having less than 0.1 EU/ml of lipopolysaccharide; genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen. The method may comprise monitoring the mammal for indications of an immune response to the purified protein fragment. In some embodiments, the immune response is a delayed type hypersensitivity response comprising erythema, swelling, or both. In some embodiments, the immune response is detected using a luminol reagent and light emission is detected. In other embodiments, the immune response is detected by a marker in blood of the mammal. For example, the blood based marker may be the release of a cytokine. In one aspect, the released cytokine is interferon-γ. Therefore, the method may comprise the steps of detecting or quantifying release of a cytokine (e.g., interferon-γ).

Yet another aspect of the disclosure is a method of eliciting and/or monitoring a T cell response in a subject. A *Toxoplasma gondii* excretory secretory antigen composition is contacted with T cells of the subject. The *Toxoplasma gondii* excretory secretory antigen composition induces a T cell response, which may involve production or secretion of cytokines. The *Toxoplasma gondii* excretory secretory antigen composition can be selected from the group consisting of: isolated and purified amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), amino acid residues 396-580 of MIC4 (SEQ ID NO: 7), and combinations thereof as elements of an antigen or components of a composition. In some embodiments, the *Toxoplasma gondii* excretory secretory antigen is devoid of contamination with lipopolysaccharide, having less than 0.1 EU/ml of lipopolysaccharide; a genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen and combinations thereof as elements of an antigen or components of a composition.

Still another aspect of the disclosure is a method of delivering a purified protein fragment of a *Toxoplasma gondii* excretory secretory antigen to a subject. An applicator device which is loaded with a purified protein fragment of a *Toxoplasma gondii* excretory secretory antigen is contacted with skin of the subject. In non-limiting examples, the applicator device may comprise one or more of a patch, a needle or a prong. The applicator device delivers the composition percutaneously. The purified protein fragment of a *Toxoplasma gondii* excretory secretory antigen is thereby delivered to the skin of the subject. The purified protein fragment comprises amino acid residues 20-340 of MIC1 (SEQ ID NO: 2), amino acid residues 320-456 of MIC1 (SEQ ID NO: 3), amino acid residues 58-231 of MIC4 (SEQ ID NO: 5), amino acid residues 217-383 of MIC4 (SEQ ID NO: 6), or amino acid residues 396-580 of MIC4 (SEQ ID NO: 7). The protein fragment is: devoid of at least N-terminal amino acids 1-19 of its corresponding full length protein MIC1 (SEQ ID NO: 1) or MIC4 (SEQ ID NO: 4); devoid of contamination with lipopolysaccharide, having less than 0.1 EU/ml of lipopolysaccharide; genetically encoded as a fusion protein; covalently attached to a moiety that enhances or facilitates purification, recombinant production, or immune cell stimulation; or in admixture with a distinct purified protein fragment of a *Toxoplasma gondii* excretory secretory antigen.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Cloning Additional Fragments of MIC1 and MIC4

Our analysis of the protein components found in ESA indicates there are >25 major proteins that are identified by mass spectrometry (1). The majority of these are micronemal proteins that are secreted in responses to elevated calcium. These proteins are involved in host cell recognition and they are recognized by antibodies from infected animals and have been extensively investigated as antigens for serological testing and as immunogens for inducing protection (2).

Our previous findings implicate the complex of MIC1-MIC4 and MIC6 as one of the major components on ESA that trigger T cell responses, including DTH responses in mouse and guinea pig. The proteins MIC1, MIC4, and MIC6 exist in a complex in *T. gondii* and they are released onto the cell surface during invasion of host cells (3). The complex is anchored by MIC6, which has a transmembrane domain (4), while MIC1 and MIC4 bind to MIC6 to form a ternary complex (5, 6). The entire complex is released into ESA by the action of an intramembrane protease that clips the transmembrane domain of MIC6 (7). Previous studies have shown that MIC4 contains 6 Apple domain repeats named for a fold that resembles an apple (5). MIC4 binds to host cells and this interaction is mediated by the C terminus containing Apple domain 6 (3). In addition, Apple domain 5 has been shown to bind to galactose found on host cell glycoproteins (5) and MIC1 also contains a lectin like domain capable of binding sialic acid (8). We have previously tested a fragment of MIC1 that comprised the N terminus without the signal peptide (beginning at residue 20) through residue 340 (FIG. 1, Table 1). This fragment, called MIC1 N term was positive in ELISPOT but not in the luminol or skin DTH assays. We cloned the C terminus (C term) of MIC1 (FIG. 1, Table 1) from the type II ME49 strain of *T. gondii* and expressed it as a N terminal SUMO fusion protein in SHuffle T7 Express *E. coli*. MIC4 is comprised of 6 apple domains that occur in tandem repeat regions.

Figure 2:
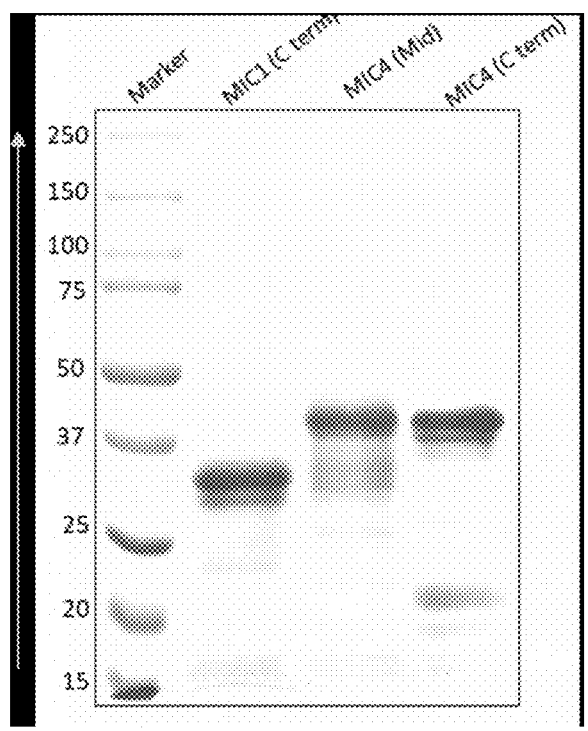
FIG. 2 shows a Coomassie blue stained SDS PAGE gel showing separation of recombinant MIC1 and MIC4 constructs. The smaller bands in lane 3 likely represent Sumo (12.5 kDa) as a breakdown product. Values on the left are molecular masses, in kilodaltons (kDa).

We have previously tested the N terminal portion of MIC4 and found that while it was active in the ELISPOT assay it did not elicit DTH responses in mouse or guinea pig. We cloned the middle portion (Mid) of MIC4 and separately the C terminal portion (C term) of MIC4 (FIG. 1, Table 1) and expressed them as a N terminal SUMO fusion proteins in SHuffle T7 Express *E. coli*. Because the C terminal portion did not express well, we codon optimized the DNA sequence for *E. coli*, without changing the protein sequence (Appendix 1). Recombinant proteins were purified and endotoxin was removed, as described previously (9). The purity and concentration of the recombinant proteins was determined by SDS-PAGE (FIG. 2).

TABLE 1

Molecular weight of recombinant MIC1 and MIC4 constructs.

| Protein fragment | Molecular weight of full length (kDa) protein | Number of amino acid in construct | Molecular weight (kDa) of tested fragment | Molecular weight (kDa) with Sumo |
|---|---|---|---|---|
| MIC1(C term) | 48.6 | 320-456 | 15 | 38 |
| MIC4 (Mid) | 63 | 217-383 | 18.2 | 41.2 |
| MIC4(C term) | 63 | 396-580 | 20.2 | 43.2 |

Example 2—Testing by ELISPOT

Figure 3:
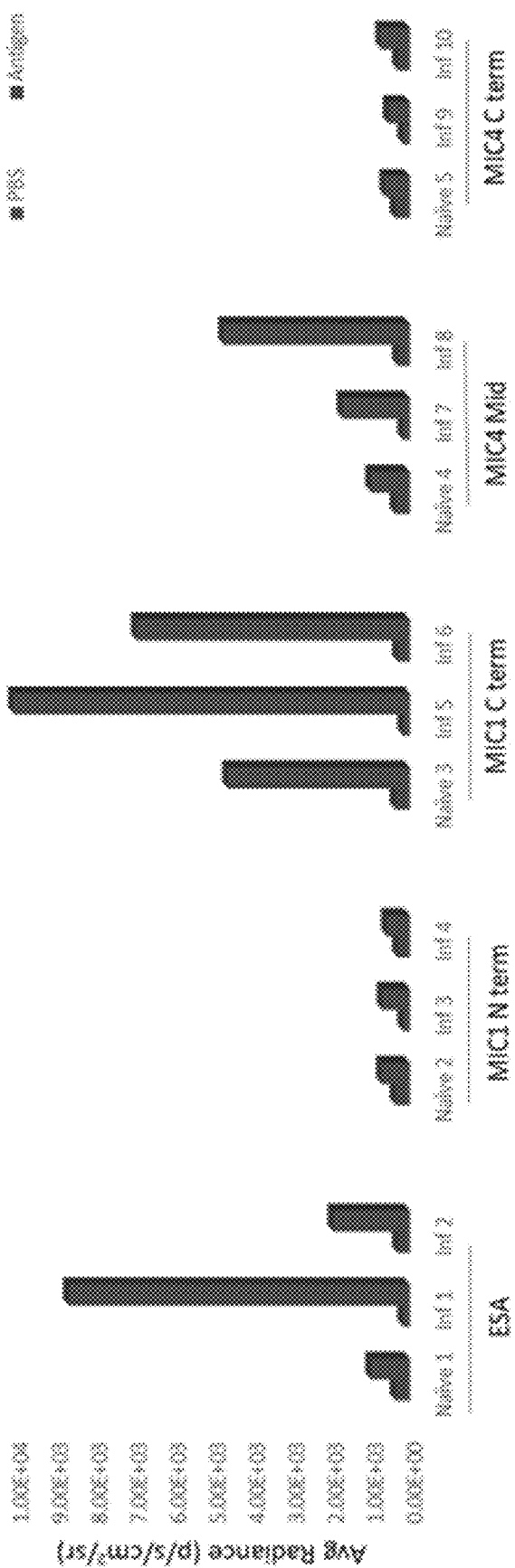
FIG. 3 shows the reaction of MIC1 and MIC4 constructs in the mouse luminol assay. Antigens were tested by ear injection with ESA as a positive control, MIC1 (N term) as a neg control, MIC1 (C term), MIC4 (Mid) and MIC4 (C term) in naïve and chronically infected mice. Plotted values are average radiance at 72 hr from the region surrounding the respective ear. Concentration of antigen used in the assay is 1.5 µg. PBS was used in the contralateral ear as a control.

The ELISPOT assay provides an efficient procedure for monitoring DTH response in vitro. Following infection, memory T cells retain the ability to respond to peptides from antigens found in the pathogen. Upon re-challenge with antigen presented by antigen-presenting cells, these memory T cells produce IFN-γ and expand to become effector cells. The ELISPOT assay measures the secretion of IFN-γ (or other cytokines) from T cells stimulated with antigen in vitro (FIG. 3). ELISPOT antigens have been described for detecting latent tuberculosis (10), and in many settings this method has replaced the conventional skin test with a product called QuantiFERON™ (11). ELISPOT assays have also been used to measure responses in patients infected with T. gondii (12), although these assays used whole crude extract of the parasite and not specific antigens.

We tested the new forms of MIC1 (C term) and MIC4 (Mid and C term) in the ELISPOT assay in parallel with preparations of the N terminus of MIC1, ESA and a Media control. Antigens were tested in two separate experiments using one naïve mouse and two mice that were chronically infected with the ME49 strain of T. gondii. Mouse splenocytes were collected 30 days after T. gondii infection and stimulated with different antigens. All of the recombinant antigens showed strong induction of IFN-γ secretion, as detected by "spots" that form when the cytokine is captured by antibodies and detected with a secondary color-reagent (Table 2). These reactions where specific to infected animals and not seen in naïve control animals (Table 2).

TABLE 2

Summary of ELISPOT response of MIC1 and MIC4 constructs.

| Sample | # Spot forming count Naive | # Spot forming count Infected |
| --- | --- | --- |
| Media | 3 ± 1 | 84 ± 12 |
| ESA | 8 ± 3 | 314 ± 50 |
| MIC1 (N term) | 75 ± 10 | 294 ± 66 |
| MIC1 (C term) | 68 ± 14 | 289 ± 52 |
| MIC4 (Mid) | 78 ± 16 | 258 ± 61 |
| MIC4 (C term) | 71 ± 9 | 264 ± 45 |

Concentration of antigen used = 0.2 µg. Data are means of IFN-γ+ spots/ 2.5 × 10⁵ cells ± SD (or variance) from one naïve and two infected mice from two experiments.

Example 3—Testing by Ear Luminol Assay

To detect DTH responses in mouse, we have used an assay that relies on light production in the skin. The basis for this method is that recruitment of monocytes and neutrophils to the site of inflammation can be detected using luminol, a substrate that gives off light when converted by myeloperoxidase (13). This method has been shown to be sensitive for detecting DTH responses in the mouse and for monitoring leukocyte influx to sites of infiltration (13). In previous studies, we have demonstrated that ESA induces positive responses in infected mice, but not naive controls. However, the previous recombinant proteins found in ESA have not shown positive reactions in this test. We tested the new forms of MIC1 (C term) and MIC4 (Mid and C term) in the luminol assay in parallel with preparations ESA. We compared naïve animals to animals that were chronically infected with the ME49 strain of T. gondii (tested at ~30 days post-infection). Both the C term portion of MIC1 and the middle (Mid) portion of MIC4 elicited positive reactions, although the reaction to MIC1 was stronger and it also elicited a reaction in the naive animal (FIG. 3).

Example 4—Testing in Guinea Pig for DTH Response

The guinea pig has been used as a model for DTH responses following injection of whole T. gondii parasite protein lysate (14). In these previous studies, chronically infected, but not naive control animals, that were injected intradermally (id) with whole antigen lysate developed erythema and swelling from 8-48 hr after injection (15). DTH positivity first appears within 1 week, but peaks at 10-15 weeks post-infection in the guinea pig (15). We have used hairless animals, as they have been shown to have fewer complications with nonspecific reactions that can occur due to the necessity of hair removal. We infected guinea pigs by oral administration of 10-50 tissue cysts of the ME49 strain of T. gondii, which is representative of the major genotype causing human disease in Europe and North America (16).

Figure 4:
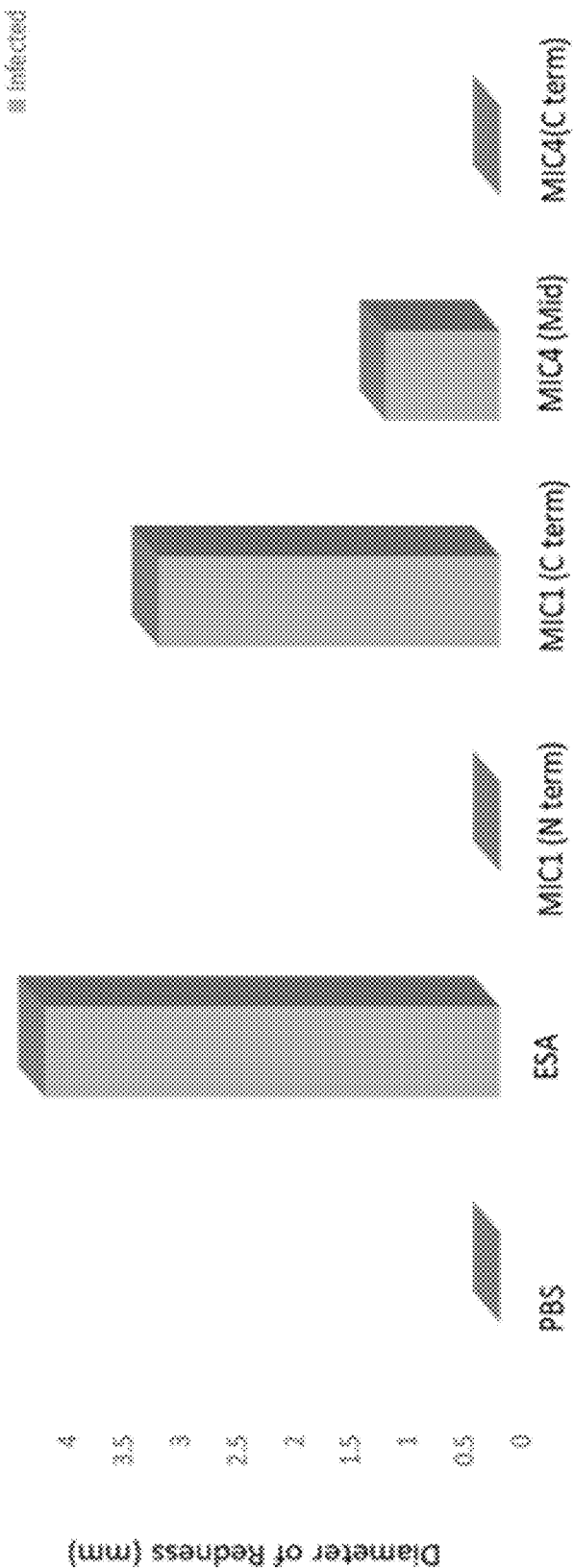
FIG. 4 shows the reaction of MIC1 and MIC4 constructs in guinea pig DTH assay. Antigens were tested by intradermal injection on the flank of naïve and chronically infected guinea pig with PBS, ESA as a positive control, MIC1 (N term) as a neg control, MIC1 (C term), MIC4 (Mid) and MIC4 (C term). Diameters of the redness was read after 24 hr. by two independent investigators. Responses from injection in the naïve guinea pig were subtracted from infected guinea pig as background. Concentration of antigen used in the assay was 10 µg. Infected, *T. gondii* infected mice; naïve, control mice.

We tested the new forms of MIC1 (C term) and MIC4 (Mid and C term) in the skin test assay in parallel with preparations ESA as a positive control and the N term of MIC1 as a negative control. Both the C term portion of MIC1 and the middle (Mid) portion of MIC4 elicited positive reactions, although the reaction to MIC1 was stronger (FIG. 4). The MIC4 C term was negative (FIG. 4).

Our findings establish that MIC1 and MIC4 are components of ESA that elicit DTH responses in infected animals. These antigens are capable of inducing IFN-□ secretion by splenic T cells (ELISPOT assay), stimulating T cells to produce cytokines that recruit inflammatory monocytes and neutrophils resulting in a positive luminol test (luminol ear assay), and eliciting a positive skin test in the guinea pig. Of the two antigens, MIC1 appears to be the most potent although the reactivity is limited to the C term fragment. This antigen also elicits non-specific reactions as positive results were seen in the mouse luminol assay in the guinea pig skin test. In the case of MIC4, it is the middle region, containing the Apple domains 3 and 4 that elicits positive responses, and no background was seen with this construct.

A sequence listing forms part of this application. Sequences included in the listing are identified below.

TABLE 3

Table of Sequences

| SEQ ID NO | Identity | Coding Type | Length | Sequence Type |
| --- | --- | --- | --- | --- |
| 1 | MIC1 FL | WT | 456 | Protein |
| 2 | MIC1 20-340 | WT | 301 | Protein |
| 3 | MIC1 320-456 | WT | 137 | Protein |
| 4 | MIC4 FL | WT | 580 | Protein |
| 5 | MIC4 20-340 | WT | 174 | Protein |
| 6 | MIC4 217-383 | WT | 167 | Protein |
| 7 | MIC4 396-580 | WT | 185 | Protein |
| 8 | MIC4 C-TERM | WT | 184 | Protein |
| 9 | MIC4 C-TERM | Codon optimized | 184 | Protein |
| 10 | MIC4 C-TERM | WT | 555 | DNA |
| 11 | MIC4 C-TERM | Codon optimized | 555 | DNA |
| 12 | MIC1 C-TERM | WT | 385 | DNA |
| 13 | MIC4 MED WT | WT | 498 | DNA |
| 14 | MIC4 MED WT | WT | 166 | Protein |
| 15 | MIC1 FULL WT | WT | 1920 | DNA |
| 16 | MIC4 FULL WT | WT | 3121 | DNA |

REFERENCES

The disclosure of each reference cited is expressly incorporated herein.

1. Brown K M, Lourido S, Sibley L D. Serum Albumin Stimulates Protein Kinase G-dependent Microneme 2. Dodangeh S, Daryani A, Sharif M, Aghayan S A, Pagheh A S, Sarvi S, Rezaei F. A systematic review on efficiency of microneme proteins to induce protective immunity against *Toxoplasma gondii*. Eur J Clin Microbiol Infect Dis. 2019; 38(4):617-629. PMID: 30680553.
3. Brecht S, Carruthers V B, Ferguson D J, Giddings O K, Wang G, Jaekle U, Harper J M, Sibley L D, Soldati D. The *Toxoplasma* micronemal protein MIC4 is an adhesin composed of six conserved apple domains. J Biol Chem. 2001; 276:4119-4127.
4. Meissner M, Reiss M, Viebig N, Carruthers V B, Toursel C, Tomavo S, Ajioka J W, Soldati D. A family of transmembrane microneme proteins of *Toxoplasma gondii* contain EGF-like domains and function as escorters. J Cell Sci. 2001; 115:563-574.
5. Marchant J, Cowper B, Liu Y, Lai L, Pinzan C, Marq J B, Friedrich N, Sawmynaden K, Liew L, Chai W, Childs R A, Saouros S, Simpson P, Roque Barreira M C, Feizi T, Soldati-Favre D, Matthews S. Galactose recognition by the apicomplexan parasite *Toxoplasma gondii*. J Biol Chem. 2012; 287(20):16720-16733. PMID: 22399295; PMC3351351
6. Saouros S, Edwards-Jones B, Reiss M, Sawmynaden K, Cota E, Simpson P, Dowse T J, Jäkle U, Ramboarina S, Shivarattan T, Matthews S, Soldati-Favre D. A novel galectin-like domain from *Toxoplasma gondii* micronemal protein 1 assists the folding, assembly, and transport of a cell adhesion complex. J Biol Chem. 2005; 280: 38583-38591.
7. Brossier F, Jewett T J, Sibley L D, Urban S. A spatially-localized rhomboid protease cleaves cell surface adhesins essential for invasion by *Toxoplasma*. Proc Natl Acad Sci (USA). 2005; 102:4146-4151.
8. Blumenschein T M, Friedrich N, Childs R A, Saouros S, Carpenter E P, Campanero-Rhodes M A, Simpson P, Chai W, Koutroukides T, Blackman M J, Feizi T, Soldati-Favre D, Matthews S. Atomic resolution insight into host cell recognition by *Toxoplasma gondii*. EMBO Journal. 2007; 26:2808-2820.
9. Saraav I, Wang Q, Brown K M, Sibley L D. Secretory Microneme Proteins Induce T-Cell Recall Responses in Mice Chronically Infected with *Toxoplasma gondii*. mSphere. 2019; 4(1). PMID: 30814319; PMC6393730.
10. Diel R, Loddenkemper R, Meywald-Walter K, Gottschalk R, Nienhaus A. Comparative performance of tuberculin skin test, QuantiFERON-TB-Gold In Tube assay, and T-Spot.TB test in contact investigations for tuberculosis. Chest. 2009; 135(4):1010-1018. PMID: 19017873.
11. Petruccioli E, Chiacchio T, Pepponi I, Vanini V, Urso R, Cuzzi G, Barcellini L, Cirillo D M, Palmieri F, Ippolito G, Goletti D. First characterization of the CD4 and CD8 T-cell responses to QuantiFERON-TB Plus. J Infect. 2016; 73(6):588-597. PMID: 27717779.
12. Hoffmann C, Ernst M, Meyer P, Wolf E, Rosenkranz T, Plettenberg A, Stoehr A, Horst H A, Marienfeld K, Lange C. Evolving characteristics of toxoplasmosis in patients infected with human immunodeficiency virus-1: clinical course and *Toxoplasma gondii*-specific immune responses. Clin Microbiol Infect. 2007; 13(5):510-515. PMID: 17298486.
13. Gross S, Gammon S T, Moss B L, Rauch D, Harding J, Heinecke J W, Ratner L, Piwnica-Worms D. Bioluminescence imaging of myeloperoxidase activity in vivo. Nature medicine. 2009; 15(4):455-461. PMID: 19305414; 2831476.
14. Frenkel J K. Dermal hypersensitivity to *toxoplasma* antigens (toxoplasmins). Proceedings Society Experimental Biology Medicine. 1948; 68:634-639.
15. Krahenbuhl J L, Blazkovec A A, Lysenko M G. In Vivo and In Vitro Studies of Delayed-Type Hypersensitivity to *Toxoplasma gondii* in Guinea Pigs. Infect Immun. 1971; 3(2):260-267. PMID:16557963; PMC416141.
16. Howe D K, Sibley L D. *Toxoplasma gondii* comprises three clonal lineages: correlation of parasite genotype with human disease. J Infect Dis. 1995; 172:1561-1566.

What is claimed is:

1. A composition comprising an antigen consisting of the amino acid sequence set forth in SEQ ID NO: 3.

2. The composition of claim 1, further comprising a protein fragment of MIC4 comprising the amino acid sequence set forth in any one of SEQ ID NO: 5, SEQ ID NO: 6, SEQ ID NO: 7, SEQ ID NO: 8, and SEQ ID NO: 14.

3. The composition of claim 1, wherein the antigen has less than 0.1 EU/ml of lipopolysaccharide.

4. The composition of claim 1, wherein the antigen is in admixture with a distinct purified protein fragment of a *Toxoplasma gondii* excretory secretory antigen.

5. A kit comprising (a) the composition of claim 1; and (b) an applicator device for administration of the composition to a subject.

6. The kit of claim 5, wherein the composition is separately packaged within the kit.

7. The kit of claim 5, wherein the applicator device is separately packaged within the kit.

8. The kit of claim 5, wherein the applicator device comprises a patch.

9. The kit of claim 5, wherein the applicator device comprises a needle.

10. The kit of claim 5, wherein the applicator device comprises a prong.

11. A method of delivering a composition comprising the composition of claim 1 to a subject, the method comprising:
    contacting an applicator device which is loaded with the composition with skin of the subject, whereby the antigen is delivered to the skin of the subject.

12. The method of claim 11, wherein the applicator device comprises a patch.

13. The method of claim 11, wherein the applicator device comprises a needle.

14. The method of claim 11, wherein the applicator device comprises a prong.

15. The method of claim 11, wherein the applicator device delivers the composition percutaneously.

* * * * *

SEQUENCE LISTING

```
<160> NUMBER OF SEQ ID NOS: 16

<210> SEQ ID NO 1
<211> LENGTH: 456
<212> TYPE: PRT
<213> ORGANISM: Toxoplasma gondii

<400> SEQUENCE: 1

Met Gly Gln Ala Leu Phe Leu Thr Val Leu Leu Pro Val Leu Phe Gly
1               5                   10                  15

Val Gly Pro Glu Ala Tyr Gly Glu Ala Ser His Ser His Ser Pro Ala
            20                  25                  30

Ser Gly Arg Tyr Ile Gln Gln Met Leu Asp Gln Arg Cys Gln Glu Ile
        35                  40                  45

Ala Ala Glu Leu Cys Gln Gly Gly Leu Arg Lys Met Cys Val Pro Ser
    50                  55                  60

Ser Arg Ile Val Ala Arg Asn Ala Val Gly Ile Thr His Gln Asn Thr
65                  70                  75                  80

Leu Glu Trp Arg Cys Phe Asp Thr Ala Ser Leu Leu Glu Ser Asn Gln
                85                  90                  95

Glu Asn Asn Gly Val Asn Cys Val Asp Asp Cys Gly His Thr Ile Pro
```

```
                100                 105                 110
Cys Pro Gly Gly Val His Arg Gln Asn Ser Asn His Ala Thr Arg His
            115                 120                 125
Glu Ile Leu Ser Lys Leu Val Glu Glu Gly Val Gln Arg Phe Cys Ser
        130                 135                 140
Pro Tyr Gln Ala Ser Ala Asn Lys Tyr Cys Asn Asp Lys Phe Pro Gly
145                 150                 155                 160
Thr Ile Ala Arg Arg Ser Lys Gly Phe Gly Asn Asn Val Glu Val Ala
                165                 170                 175
Trp Arg Cys Tyr Glu Lys Ala Ser Leu Leu Tyr Ser Val Tyr Ala Glu
            180                 185                 190
Cys Ala Ser Asn Cys Gly Thr Thr Trp Tyr Cys Pro Gly Gly Arg Arg
        195                 200                 205
Gly Thr Ser Thr Glu Leu Asp Lys Arg His Tyr Thr Glu Glu Glu Gly
        210                 215                 220
Ile Arg Gln Ala Ile Gly Ser Val Asp Ser Pro Cys Ser Glu Val Glu
225                 230                 235                 240
Val Cys Leu Pro Lys Asp Glu Asn Pro Pro Val Cys Leu Asp Glu Ser
                245                 250                 255
Gly Gln Ile Ser Arg Thr Gly Gly Pro Pro Ser Gln Pro Pro Glu
            260                 265                 270
Met Gln Gln Pro Ala Asp Arg Ser Asp Glu Arg Gly Gly Lys Glu
        275                 280                 285
Gln Ser Pro Gly Gly Glu Ala Gln Pro Asp His Pro Thr Lys Gly Gly
        290                 295                 300
Asn Ile Asp Leu Pro Glu Lys Ser Thr Ser Pro Glu Lys Thr Pro Lys
305                 310                 315                 320
Thr Glu Ile His Gly Asp Ser Thr Lys Ala Thr Leu Glu Glu Gly Gln
                325                 330                 335
Gln Leu Thr Leu Thr Phe Ile Ser Thr Lys Leu Asp Val Ala Val Gly
            340                 345                 350
Ser Cys His Ser Leu Val Ala Asn Phe Leu Asp Gly Phe Leu Lys Phe
        355                 360                 365
Gln Thr Gly Ser Asn Ser Ala Phe Asp Val Val Glu Val Glu Glu Pro
        370                 375                 380
Ala Gly Pro Ala Val Leu Thr Ile Gly Leu Gly His Lys Gly Arg Leu
385                 390                 395                 400
Ala Val Val Leu Asp Tyr Thr Arg Leu Asn Ala Ala Leu Gly Ser Ala
                405                 410                 415
Ala Tyr Val Val Glu Asp Ser Gly Cys Ser Ser Glu Glu Val Ser
            420                 425                 430
Phe Gln Gly Val Gly Ser Gly Ala Thr Leu Val Val Thr Thr Leu Gly
        435                 440                 445
Glu Ser Pro Thr Ala Val Ser Ala
    450                 455

<210> SEQ ID NO 2
<211> LENGTH: 301
<212> TYPE: PRT
<213> ORGANISM: Artificial Sequence
<220> FEATURE:
<223> OTHER INFORMATION: Synthesized

<400> SEQUENCE: 2

Glu Ala Tyr Gly Glu Ala Ser His Ser His Ser Pro Ala Ser Gly Arg
```

```
                1               5                      10                      15
        Tyr Ile Gln Gln Met Leu Asp Gln Arg Cys Gln Glu Ile Ala Ala Glu
                        20                      25                      30

Leu Cys Gln Gly Gly Leu Arg Lys Met Cys Val Pro Ser Ser Arg Ile
                        35                      40                      45

Val Ala Arg Asn Ala Val Gly Ile Thr His Gln Asn Thr Leu Glu Trp
         50                      55                      60

Arg Cys Phe Asp Thr Ala Ser Leu Leu Glu Ser Asn Gln Glu Asn Asn
         65                      70                      75                      80

Gly Val Asn Cys Val Asp Asp Cys Gly His Thr Ile Pro Cys Pro Gly
                        85                      90                      95

Gly Val His Arg Gln Asn Ser Asn His Ala Thr Arg His Glu Ile Leu
                        100                     105                     110

Ser Lys Leu Val Glu Glu Gly Val Gln Arg Phe Cys Ser Pro Tyr Gln
                        115                     120                     125

Ala Ser Ala Asn Lys Tyr Cys Asn Asp Lys Phe Pro Gly Thr Ile Ala
                        130                     135                     140

Arg Arg Ser Lys Gly Phe Gly Asn Asn Val Glu Val Ala Trp Arg Cys
         145                     150                     155                     160

Tyr Glu Lys Ala Ser Leu Leu Tyr Ser Val Tyr Ala Glu Cys Ala Ser
                        165                     170                     175

Asn Cys Gly Thr Thr Trp Tyr Cys Pro Gly Gly Arg Arg Gly Thr Ser
                        180                     185                     190

Thr Glu Leu Asp Lys Arg His Tyr Thr Glu Glu Glu Gly Ile Arg Gln
                        195                     200                     205

Ala Ile Gly Ser Val Asp Ser Pro Cys Ser Glu Val Glu Val Cys Leu
         210                     215                     220

Pro Lys Asp Glu Asn Pro Pro Val Cys Leu Asp Glu Ser Gly Gln Ile
         225                     230                     235                     240

Ser Arg Thr Gly Gly Pro Pro Ser Gln Pro Pro Glu Met Gln Gln
                        245                     250                     255

Pro Ala Asp Arg Ser Asp Glu Arg Gly Gly Lys Glu Gln Ser Pro
                        260                     265                     270

Gly Gly Glu Ala Gln Pro Asp His Pro Thr Lys Gly Gly Asn Ile Asp
                        275                     280                     285

Leu Pro Glu Lys Ser Thr Ser Pro Glu Lys Thr Pro Lys
                        290                     295                     300

<210> SEQ ID NO 3
<211> LENGTH: 137
<212> TYPE: PRT
<213> ORGANISM: Artificial Sequence
<220> FEATURE:
<223> OTHER INFORMATION: Synthesize

<400> SEQUENCE: 3

Lys Thr Glu Ile His Gly Asp Ser Thr Lys Ala Thr Leu Glu Glu Gly
         1               5                      10                      15

Gln Gln Leu Thr Leu Thr Phe Ile Ser Thr Lys Leu Asp Val Ala Val
                        20                      25                      30

Gly Ser Cys His Ser Leu Val Ala Asn Phe Leu Asp Gly Phe Leu Lys
                        35                      40                      45

Phe Gln Thr Gly Ser Asn Ser Ala Phe Asp Val Val Glu Val Glu Glu
         50                      55                      60

Pro Ala Gly Pro Ala Val Leu Thr Ile Gly Leu Gly His Lys Gly Arg
```

```
                65                   70                  75                  80
Leu Ala Val Val Leu Asp Tyr Thr Arg Leu Asn Ala Ala Leu Gly Ser
                        85                  90                  95

Ala Ala Tyr Val Val Glu Asp Ser Gly Cys Ser Ser Glu Glu Val
                100                 105                 110

Ser Phe Gln Gly Val Gly Ser Gly Ala Thr Leu Val Thr Thr Leu
                115                 120                 125

Gly Glu Ser Pro Thr Ala Val Ser Ala
        130                 135

<210> SEQ ID NO 4
<211> LENGTH: 580
<212> TYPE: PRT
<213> ORGANISM: Toxoplasma gondii

<400> SEQUENCE: 4

Met Arg Ala Ser Leu Pro Val His Leu Val Val Cys Thr Gln Leu Ser
1               5                   10                  15

Ala Val Trp Phe Gly Val Ala Lys Ala His Gly Gly His Arg Leu Glu
                20                  25                  30

Pro His Val Pro Gly Phe Leu Gln Gly Phe Thr Asp Ile Thr Pro Ala
            35                  40                  45

Gly Asp Asp Val Ser Ala Asn Val Thr Ser Ser Glu Pro Ala Lys Leu
        50                  55                  60

Asp Leu Ser Cys Val His Ser Asp Asn Lys Gly Ser Arg Ala Pro Thr
65                  70                  75                  80

Ile Gly Glu Pro Val Pro Asp Val Ser Leu Glu Gln Cys Ala Ala Gln
                85                  90                  95

Cys Lys Ala Val Asp Gly Cys Thr His Phe Thr Tyr Asn Asp Asp Ser
                100                 105                 110

Lys Met Cys His Val Lys Glu Gly Lys Pro Asp Leu Tyr Asp Leu Thr
            115                 120                 125

Gly Gly Lys Thr Ala Ser Arg Ser Cys Asp Arg Ser Cys Phe Glu Gln
        130                 135                 140

His Val Ser Tyr Glu Gly Ala Pro Asp Val Met Thr Ala Met Val Thr
145                 150                 155                 160

Ser Gln Ser Ala Asp Cys Gln Ala Ala Cys Ala Ala Asp Pro Ser Cys
                165                 170                 175

Glu Ile Phe Thr Tyr Asn Glu His Asp Gln Lys Cys Thr Phe Lys Gly
                180                 185                 190

Arg Gly Phe Ser Ala Phe Lys Glu Arg Gly Val Leu Gly Val Thr Ser
            195                 200                 205

Gly Pro Lys Gln Phe Cys Asp Glu Gly Gly Lys Leu Thr Gln Glu Glu
        210                 215                 220

Met Glu Asp Gln Ile Ser Gly Cys Ile Gln Leu Ser Asp Val Gly Ser
225                 230                 235                 240

Met Thr Ala Asp Leu Glu Glu Pro Met Glu Ala Asp Ser Val Gly Ala
                245                 250                 255

Cys Met Glu Arg Cys Arg Cys Asp Gly Arg Cys Thr His Phe Thr Phe
                260                 265                 270

Asn Asp Asn Thr Arg Met Cys Tyr Leu Lys Gly Asp Lys Met Gln Leu
            275                 280                 285

Tyr Ser Ser Pro Gly Asp Arg Thr Gly Pro Lys Ser Cys Asp Ser Ser
        290                 295                 300
```

```
Cys Phe Ser Asn Gly Val Ser Tyr Val Asp Pro Ala Thr Asp Val
305                 310                 315                 320

Glu Thr Val Phe Glu Ile Ser His Pro Ile Tyr Cys Gln Val Ile Cys
            325                 330                 335

Ala Ala Asn Pro Leu Cys Thr Val Phe Gln Trp Tyr Ala Ser Glu Ala
            340                 345                 350

Lys Cys Val Val Lys Arg Lys Gly Phe Tyr Lys His Arg Lys Thr Gly
            355                 360                 365

Val Thr Gly Val Thr Val Gly Pro Arg Glu Phe Cys Asp Phe Gly Gly
        370                 375                 380

Ser Ile Arg Asp Arg Glu Glu Ala Asp Ala Val Gly Ser Asp Asp Gly
385                 390                 395                 400

Leu Asn Ala Glu Ala Thr Met Ala Asn Ser Pro Asp Phe His Asp Glu
                405                 410                 415

Val Glu Cys Val His Thr Gly Asn Ile Gly Ser Lys Ala Gln Thr Ile
            420                 425                 430

Gly Glu Val Lys Arg Ala Ser Ser Leu Ser Glu Cys Arg Ala Arg Cys
            435                 440                 445

Gln Ala Glu Lys Glu Cys Ser His Tyr Thr Tyr Asn Val Lys Ser Gly
450                 455                 460

Leu Cys Tyr Pro Lys Arg Gly Lys Pro Gln Phe Tyr Lys Tyr Leu Gly
465                 470                 475                 480

Asp Met Thr Gly Ser Arg Thr Cys Asp Thr Ser Cys Leu Arg Arg Gly
                485                 490                 495

Val Asp Tyr Ser Gln Gly Pro Glu Val Gly Lys Pro Trp Tyr Ser Thr
            500                 505                 510

Leu Pro Thr Asp Cys Gln Val Ala Cys Asp Ala Glu Asp Ala Cys Leu
        515                 520                 525

Val Phe Thr Trp Asp Ser Ala Thr Ser Arg Cys Tyr Leu Ile Gly Ser
        530                 535                 540

Gly Phe Ser Ala His Arg Arg Asn Asp Val Asp Gly Val Val Ser Gly
545                 550                 555                 560

Pro Tyr Thr Phe Cys Asp Asn Gly Glu Asn Leu Gln Val Leu Glu Ala
                565                 570                 575

Lys Asp Thr Glu
            580

<210> SEQ ID NO 5
<211> LENGTH: 174
<212> TYPE: PRT
<213> ORGANISM: Artificial Sequence
<220> FEATURE:
<223> OTHER INFORMATION: Synthesized

<400> SEQUENCE: 5

Ser Ser Glu Pro Ala Lys Leu Asp Leu Ser Cys Val His Ser Asp Asn
1               5                   10                  15

Lys Gly Ser Arg Ala Pro Thr Ile Gly Glu Pro Val Pro Asp Val Ser
            20                  25                  30

Leu Glu Gln Cys Ala Ala Gln Cys Lys Ala Val Asp Gly Cys Thr His
        35                  40                  45

Phe Thr Tyr Asn Asp Asp Ser Lys Met Cys His Val Lys Glu Gly Lys
    50                  55                  60

Pro Asp Leu Tyr Asp Leu Thr Gly Gly Lys Thr Ala Ser Arg Ser Cys
65                  70                  75                  80
```

```
Asp Arg Ser Cys Phe Glu Gln His Val Ser Tyr Glu Gly Ala Pro Asp
                85                  90                  95

Val Met Thr Ala Met Val Thr Ser Gln Ser Ala Asp Cys Gln Ala Ala
            100                 105                 110

Cys Ala Ala Asp Pro Ser Cys Glu Ile Phe Thr Tyr Asn Glu His Asp
        115                 120                 125

Gln Lys Cys Thr Phe Lys Gly Arg Gly Phe Ser Ala Phe Lys Glu Arg
    130                 135                 140

Gly Val Leu Gly Val Thr Ser Gly Pro Lys Gln Phe Cys Asp Glu Gly
145                 150                 155                 160

Gly Lys Leu Thr Gln Glu Glu Met Glu Asp Gln Ile Ser Gly
                165                 170
```

<210> SEQ ID NO 6
<211> LENGTH: 167
<212> TYPE: PRT
<213> ORGANISM: Artificial Sequence
<220> FEATURE:
<223> OTHER INFORMATION: Synthesized

<400> SEQUENCE: 6

```
Gly Gly Lys Leu Thr Gln Glu Glu Met Glu Asp Gln Ile Ser Gly Cys
1               5                   10                  15

Ile Gln Leu Ser Asp Val Gly Ser Met Thr Ala Asp Leu Glu Glu Pro
            20                  25                  30

Met Glu Ala Asp Ser Val Gly Ala Cys Met Glu Arg Cys Arg Cys Asp
        35                  40                  45

Gly Arg Cys Thr His Phe Thr Phe Asn Asp Asn Thr Arg Met Cys Tyr
    50                  55                  60

Leu Lys Gly Asp Lys Met Gln Leu Tyr Ser Ser Pro Gly Asp Arg Thr
65                  70                  75                  80

Gly Pro Lys Ser Cys Asp Ser Ser Cys Phe Ser Asn Gly Val Ser Tyr
                85                  90                  95

Val Asp Asp Pro Ala Thr Asp Val Glu Thr Val Phe Glu Ile Ser His
            100                 105                 110

Pro Ile Tyr Cys Gln Val Ile Cys Ala Ala Asn Pro Leu Cys Thr Val
        115                 120                 125

Phe Gln Trp Tyr Ala Ser Glu Ala Lys Cys Val Val Lys Arg Lys Gly
    130                 135                 140

Phe Tyr Lys His Arg Lys Thr Gly Val Thr Gly Val Thr Val Gly Pro
145                 150                 155                 160

Arg Glu Phe Cys Asp Phe Gly
                165
```

<210> SEQ ID NO 7
<211> LENGTH: 185
<212> TYPE: PRT
<213> ORGANISM: Artificial Sequence
<220> FEATURE:
<223> OTHER INFORMATION: Synthesized

<400> SEQUENCE: 7

```
Gly Ser Asp Asp Gly Leu Asn Ala Glu Ala Thr Met Ala Asn Ser Pro
1               5                   10                  15

Asp Phe His Asp Glu Val Glu Cys Val His Thr Gly Asn Ile Gly Ser
            20                  25                  30

Lys Ala Gln Thr Ile Gly Glu Val Lys Arg Ala Ser Ser Leu Ser Glu
        35                  40                  45
```

```
Cys Arg Ala Arg Cys Gln Ala Glu Lys Glu Cys Ser His Tyr Thr Tyr
        50                  55                  60

Asn Val Lys Ser Gly Leu Cys Tyr Pro Lys Arg Gly Lys Pro Gln Phe
 65                  70                  75                  80

Tyr Lys Tyr Leu Gly Asp Met Thr Gly Ser Arg Thr Cys Asp Thr Ser
                    85                  90                  95

Cys Leu Arg Arg Gly Val Asp Tyr Ser Gln Gly Pro Glu Val Gly Lys
                100                 105                 110

Pro Trp Tyr Ser Thr Leu Pro Thr Asp Cys Gln Val Ala Cys Asp Ala
            115                 120                 125

Glu Asp Ala Cys Leu Val Phe Thr Trp Asp Ser Ala Thr Ser Arg Cys
130                 135                 140

Tyr Leu Ile Gly Ser Gly Phe Ser Ala His Arg Arg Asn Asp Val Asp
145                 150                 155                 160

Gly Val Val Ser Gly Pro Tyr Thr Phe Cys Asp Asn Gly Glu Asn Leu
                165                 170                 175

Gln Val Leu Glu Ala Lys Asp Thr Glu
            180                 185

<210> SEQ ID NO 8
<211> LENGTH: 184
<212> TYPE: PRT
<213> ORGANISM: Toxoplasma gondii

<400> SEQUENCE: 8

Ser Asp Asp Gly Leu Asn Ala Glu Ala Thr Met Ala Asn Ser Pro Asp
 1               5                  10                  15

Phe His Asp Glu Val Glu Cys Val His Thr Gly Asn Ile Gly Ser Lys
                20                  25                  30

Ala Gln Thr Ile Gly Glu Val Lys Arg Ala Ser Ser Leu Ser Glu Cys
            35                  40                  45

Arg Ala Arg Cys Gln Ala Glu Lys Glu Cys Ser His Tyr Thr Tyr Asn
 50                  55                  60

Val Lys Ser Gly Leu Cys Tyr Pro Lys Arg Gly Lys Pro Gln Phe Tyr
 65                  70                  75                  80

Lys Tyr Leu Gly Asp Met Thr Gly Ser Arg Thr Cys Asp Thr Ser Cys
                85                  90                  95

Leu Arg Arg Gly Val Asp Tyr Ser Gln Gly Pro Glu Val Gly Lys Pro
            100                 105                 110

Trp Tyr Ser Thr Leu Pro Thr Asp Cys Gln Val Ala Cys Asp Ala Glu
        115                 120                 125

Asp Ala Cys Leu Val Phe Thr Trp Asp Ser Ala Thr Ser Arg Cys Tyr
130                 135                 140

Leu Ile Gly Ser Gly Phe Ser Ala His Arg Arg Asn Asp Val Asp Gly
145                 150                 155                 160

Val Val Ser Gly Pro Tyr Thr Phe Cys Asp Asn Gly Glu Asn Leu Gln
                165                 170                 175

Val Leu Glu Ala Lys Asp Thr Glu
            180

<210> SEQ ID NO 9
<211> LENGTH: 184
<212> TYPE: PRT
<213> ORGANISM: Toxoplasma gondii

<400> SEQUENCE: 9
```

```
Ser Asp Asp Gly Leu Asn Ala Glu Ala Thr Met Ala Asn Ser Pro Asp
1               5                   10                  15

Phe His Asp Glu Val Glu Cys Val His Thr Gly Asn Ile Gly Ser Lys
            20                  25                  30

Ala Gln Thr Ile Gly Glu Val Lys Arg Ala Ser Ser Leu Ser Glu Cys
        35                  40                  45

Arg Ala Arg Cys Gln Ala Glu Lys Cys Ser His Tyr Thr Tyr Asn
    50                  55                  60

Val Lys Ser Gly Leu Cys Tyr Pro Lys Arg Gly Lys Pro Gln Phe Tyr
65              70                  75                  80

Lys Tyr Leu Gly Asp Met Thr Gly Ser Arg Thr Cys Asp Thr Ser Cys
                85                  90                  95

Leu Arg Arg Gly Val Asp Tyr Ser Gln Gly Pro Glu Val Gly Lys Pro
            100                 105                 110

Trp Tyr Ser Thr Leu Pro Thr Asp Cys Gln Val Ala Cys Asp Ala Glu
        115                 120                 125

Asp Ala Cys Leu Val Phe Thr Trp Asp Ser Ala Thr Ser Arg Cys Tyr
    130                 135                 140

Leu Ile Gly Ser Gly Phe Ser Ala His Arg Arg Asn Asp Val Asp Gly
145             150                 155                 160

Val Val Ser Gly Pro Tyr Thr Phe Cys Asp Asn Gly Glu Asn Leu Gln
                165                 170                 175

Val Leu Glu Ala Lys Asp Thr Glu
            180

<210> SEQ ID NO 10
<211> LENGTH: 555
<212> TYPE: DNA
<213> ORGANISM: Toxoplasma gondii

<400> SEQUENCE: 10
tcagacgatg gcctcaacgc ggaagcaact atggcaaatt ctcctgattt tcacgacgaa      60
gtagaatgcg tccacacggg caacattggg tcaaaagcac aaaccattgg agaagtgaaa     120
cgcgcaagta gtttgagtga gtgcagagcc agatgccaag cggagaaaga atgcagccac     180
tacacttaca atgtaaaatc cggtttgtgt tatccaaaaa gaggaaagcc tcaattttat     240
aagtatcttg gcgacatgac gggatccaga acatgtgata caagttgcct taggagggga     300
gtcgattact cacagggccc tgaagtagga aagccttggt attctacgct gccgacagac     360
tgccaagttg catgcgacgc tgaggatgct tgcctggtgt tcacctggga ttcggcgacg     420
tcacgatgct acctcatcgg ctcaggtttc tcggcacatc gacggaacga cgtggatggc     480
gtggtatctg gaccctatac tttctgtgac aatggcgaaa accttcaggt gcttgaagcg     540
aaagacacag aatga                                                     555

<210> SEQ ID NO 11
<211> LENGTH: 555
<212> TYPE: DNA
<213> ORGANISM: Toxoplasma gondii

<400> SEQUENCE: 11
agtgatgatg gtctgaatgc cgaagcaacc atggcaaata gtccggattt tcatgatgaa      60
gttgaatgcg ttcataccgg taatattggt agcaaagcac agaccattgg tgaagttaaa     120
cgtgcaagca gcctgagcga atgtcgtgca cgttgtcagg cagaaaaaga atgtagccat     180
```

```
tatacctaca acgtgaaaag cggtctgtgt tatccgaaac gtggtaaacc gcagttttac    240
aaatatctgg gtgatatgac cggtagccgt acctgtgata ccagctgtct gcgtcgtggt    300
gttgattatt cacagggtcc tgaagtgggt aaaccgtggt atagcaccct gccgaccgat    360
tgtcaggttg catgtgatgc agaagatgcc tgtctggttt ttacctggga tagcgcaacc    420
agccgttgtt atctgattgg tagcggtttt agcgcacatc gtcgtaatga tgttgatggt    480
gttgttagcg gtccgtatac cttttgtgat aatggtgaaa atctgcaggt tctggaagca    540
aaagataccg aataa                                                    555

<210> SEQ ID NO 12
<211> LENGTH: 385
<212> TYPE: DNA
<213> ORGANISM: Toxoplasma gondii

<400> SEQUENCE: 12
agcgacgctc gaagaggggc agcaactaac gctcacgttt atctccacta aactggatgt     60
tgctgtaggc tcgtgtcatt cactcgtcgc gaatttcctt gatggatttt tgaagtttca    120
gacgggctca aattcggcgt tcgatgtggt agaagtggaa gagccagcag acccgcagt     180 gcttacgata ggtctgggac acaaaggccg tctcgctgtt gtcctcgact acaccaggct    240
caatgctgct ttaggatcag ctgcttacgt ggtcgaagat tctggatgca gctcaagtga    300
agaggttagt ttccaaggag tgggtagtgg agcgacgctc gtggtgacga cgcttggcga    360
gagtcctacg gccgtctctg cttga                                         385

<210> SEQ ID NO 13
<211> LENGTH: 498
<212> TYPE: DNA
<213> ORGANISM: Toxoplasma gondii

<400> SEQUENCE: 13
ggtaaattaa ctcaagagga gatggaagat cagatcagtg gctgcattca attgagtgac     60
gttggatcaa tgactgctga cctggaggag cctatggagg ctgattctgt tggcgcttgt    120
atggaacggt gccgctgtga tggaagatgc acgcacttca cgttcaacga taatactcgg    180
atgtgctacc tcaaaggtga caagatgcag ttgtactcat ctccaggtga cagaaccggc    240
ccaaagagct gcgattcaag ctgcttctcg aacggggttt cttacgtcga tgatccggcg    300
acagatgttg agaccgtatt cgaaatttca cacccaattt attgtcaagt aatctgcgcc    360
gcaaatccgt tgtgtacagt gtttcagtgg tatgcctccg aggcaaagtg cgtcgtcaag    420 agaaagggt tttacaaaca cagaaaaaca ggtgtcacgg gagtcacagt gggccctcgg    480
gagttctgcg attttggc                                                 498

<210> SEQ ID NO 14
<211> LENGTH: 166
<212> TYPE: PRT
<213> ORGANISM: Toxoplasma gondii

<400> SEQUENCE: 14

Gly Lys Leu Thr Gln Glu Glu Met Glu Asp Gln Ile Ser Gly Cys Ile
1               5                   10                  15

Gln Leu Ser Asp Val Gly Ser Met Thr Ala Asp Leu Glu Glu Pro Met
            20                  25                  30

Glu Ala Asp Ser Val Gly Ala Cys Met Glu Arg Cys Arg Cys Asp Gly
        35                  40                  45
```

```
Arg Cys Thr His Phe Thr Phe Asn Asp Asn Thr Arg Met Cys Tyr Leu
    50                  55                  60

Lys Gly Asp Lys Met Gln Leu Tyr Ser Ser Pro Gly Asp Arg Thr Gly
65                  70                  75                  80

Pro Lys Ser Cys Asp Ser Ser Cys Phe Ser Asn Gly Val Ser Tyr Val
                85                  90                  95

Asp Asp Pro Ala Thr Asp Val Glu Thr Val Phe Glu Ile Ser His Pro
            100                 105                 110

Ile Tyr Cys Gln Val Ile Cys Ala Ala Asn Pro Leu Cys Thr Val Phe
        115                 120                 125

Gln Trp Tyr Ala Ser Glu Ala Lys Cys Val Val Lys Arg Lys Gly Phe
    130                 135                 140

Tyr Lys His Arg Lys Thr Gly Val Thr Gly Val Thr Val Gly Pro Arg
145                 150                 155                 160

Glu Phe Cys Asp Phe Gly
                165

<210> SEQ ID NO 15
<211> LENGTH: 1920
<212> TYPE: DNA
<213> ORGANISM: Toxoplasma gondii

<400> SEQUENCE: 15
acctgaaagc gggtgccgcg tcgctaccgt ttcctgtggc gtctctagtg cgacatccga      60
agtaacagta acgtccggca tggaacgccg acgcgggtgt tccagtcgcc tggctccttc     120
tactcgcact tcgatgttac gttccttatt ggtgcgacgc ggttctcgtg ttgctagacg     180
tcgcaccggc tgaaagctgt agaaaattta gttattttcc tgtcagctag cttgcaggag     240
tgcgtttttg tgtgttggtt tcgtctcaca tggctgctga tctgttgatg cagctgtgta     300
cacgtgcctc gattctgtag ttgacctaga acggatttgc aaagatgggc aggcgttgt      360 ttctcaccgt tctattgccg tgttatttg gcgtgggcc agaagcatat ggagaagcgt       420
cgcattctca ttcgccggca tcgggacgtt atatacaaca gatgcttgac caacgctgcc     480
aagagattgc tgcagaactc tgccaaggcg gacttcgtaa aatgtgtgtg ccctctagcc     540
ggatagtagc tcgaaacgcc gtgggcatta tcatcaaaa tacacttgaa tggagatgct      600
ttgatacagc tctttgctg gagagcaatc aagaaaacaa cggtgttaat tgcgtggacg      660
actgtggcca cacgataccg tgtcctggcg gcgtacaccg gcaaacagt aatcacgcaa      720 cgcgccatga gatactgtcc aaattggtcg aagaaggagt acaacggttc tgcagtcctt     780
atcaagcatc tgccaacaag tactgtaacg acaaatttcc agggaccatt gcgaggaggt     840
cgaagggctt cggaaacaat gtcgaggttg cgtggaggtg ttacgagaag gccagcttgc     900
tgtactcggt ttatgctgag tgtgcgagca actgcggaac aacgtggtac tgccctggag     960
gacgacgagg gacgtcgaca gaactagaca agcggcatta tacagaagag gaaggaattc    1020
gccaggcaat cggatccgtc gacagcccat gttctgaagt tgaagtctgc ctaccgaagg    1080
atgagaatcc cccggtgtgt ttagatgaaa gtggccagat tcacgaact ggtggtgggc     1140 caccgtcaca accgcctgag atgcaacagc ccgccgatcg ttcggacgag agaggtggcg    1200
gtaaggaaca gtcgcctgga ggagaagctc agccggacca tccaacgaag ggtggtaaca    1260
tagacctgcc tgagaaatca acatctcccg agaagacgcc gaaaaccgag atccatggtg    1320
acagcacgaa agcgacgctc gaagaggggc agcaactaac gctcacgttt atctccacta    1380
aactggatgt tgctgtaggc tcgtgtcatt cactcgtcgc gaatttcctt gatggatttt    1440
```

```
tgaagtttca gacgggctca aattcggcgt tcgatgtggt agaagtggaa gagccagcag    1500
gacccgcagt gcttacgata ggtctgggac acaaaggccg tctcgctgtt gtcctcgact    1560
acaccaggct caatgctgct ttaggatcag ctgcttacgt ggtcgaagat tctggatgca    1620
gctcaagtga agaggttagt ttccaaggag tgggtagtgg agcgacgctc gtggtgacga    1680
cgcttggcga gagtcctacg gccgtctctg cttgatttat agtactcttt ggagcatgct    1740
tgtggaggaa cgggacaatc tcggcaaaat caggatgaag tttgtgagat acagatcgtt    1800
cctgaacagt ggaagatgcg tcactattac acctatatgc gtcctggttc ttgtagagtt    1860
ggagttcttg caggtgtaat gactatgaca tacggatata acttcatacg gggaactgtg    1920

<210> SEQ ID NO 16
<211> LENGTH: 3121
<212> TYPE: DNA
<213> ORGANISM: Toxoplasma gondii

<400> SEQUENCE: 16
ttttctgtgc atctgtgctg caaaacgggc ctctgtgcat tatttcccca ccaacaattg      60
ccgcgtcgat ccgggtcccg ctcaagctct gcagaactag gctctcgata tagatcagta     120
caatcattcg cttctgacaa tcgcatcgac tgagcgacgc gttgatcgtc gactgtcgtg     180
cgtcgcattc gggcatctcg aaccggtgtt gattccctgt gtcattattt cacttccgtc     240
cttctctcgt ggcgatctat aatacgcgtg tgttgttgcg tgcattgctt gtgttgttgt     300
ggatgtgttt tcttttgtga ccgctcacga acaccccacg caaaatgaga gcgtcgctcc     360
cggttcacct cgttgtgtgc acgcagctaa gtgccgtttg gtttggagtg gctaaagccc     420
atggtggaca ccgactggaa ccgcatgttc ccggattcct gcaaggcttc actgatatca     480
cgcctgcagg tgatgacgtt agtgccaacg taacaagttc ggagcctgca aaacttgatc     540
tctcttgtgt gcactctgac aataagggat caagggctcc cacaataggc gagccagtgc     600
cagatgtgtc cctgaacaa tgtgctgcgc aatgcaaggc tgttgatggc tgcacacatt      660
tcacttataa tgacgattcg aagatgtgcc atgtgaagga gggaaaaccc gatttatacg     720
atctcacagg aggcaaaaca gcatcgcgca gttgcgatag atcatgcttc gaacaacacg     780
tatcgtatga gggagctcct gacgtgatga cagcgatggt cacgagccag tcagcggact     840
gtcaggctgc gtgtgcggct gacccgagct gcgagatctt cacttataac gaacacgacc     900
agaaatgtac tttcaaagga aggggtttt ctgcgtttaa ggaacgaggg gtgttgggtg      960
tgacttccgg gccgaaacag ttctgcgatg aaggcggtaa attaactcaa gaggagatgg    1020
aagatcagat cagtggctgc attcaattga gtgacgttgg atcaatgact gctgacctgg    1080
aggagcctat ggaggctgat tctgttggcg cttgtatgga acggtgccgc tgtgatggaa    1140
gatgcacgca cttcacgttc aacgataata ctcggatgtg ctacctcaaa ggtgacaaga    1200
tgcagttgta ctcatctcca ggtgacagaa ccggcccaaa gagctgcgat tcaagctgct    1260
tctcgaacgg ggtttcttac gtcgatgatc cggcgacaga tgttgagacc gtattcgaaa    1320
tttcacaccc aatttattgt caagtaatct gcgccgcaaa tccgttgtgt acagtgtttc    1380
agtggtatgc ctccgaggca aagtgcgtcg tcaagagaaa ggggttttac aaacacagaa    1440
aaacaggtgt cacgggagtc acagtgggcc ctcgggagtt ctgcgatttt ggcggtagca    1500
tccgcgaccg agaagaggca gacgccgttg gatcagacga tggcctcaac gcggaagcaa    1560
ctatggcaaa ttctcctgat tttcacgacg aagtagaatg cgtccacacg ggcaacattg    1620
```

-continued

```
ggtcaaaagc acaaaccatt ggagaagtga aacgcgcaag tagtttgagt gagtgcagag  1680
ccagatgcca agcggagaaa gaatgcagcc actacactta caatgtaaaa tccggtttgt  1740
gttatccaaa aagaggaaag cctcaatttt ataagtatct tggcgacatg acgggatcca  1800
gaacatgtga tacaagttgc cttaggaggg gagtcgatta ctcacagggc cctgaagtag  1860
gaaagccttg gtattctacg ctgccgacag actgccaagt tgcatgcgac gctgaggatg  1920
cttgcctggt gttcacctgg gattcggcga cgtcacgatg ctacctcatc ggctcaggtt  1980
tctcggcaca tcgacggaac gacgtggatg gcgtggtatc tggaccctat actttctgtg  2040
acaatggcga aaaccttcag gtgcttgaag cgaaagacac agaatgaccc aggagggtgc  2100
cagatacttt gtgtgactgc gacatgcagt catgtactca aagtgttgta catggacagg  2160
aggacttttt ttttaagtca ttgcagaggt gcgttttcgg agcagcacta taactgcgtc  2220
agcgactaag cacgccacgt agctgaatga aacgcagcca ccttcgtgta tgtatgcttc  2280
gtttttttgtc gctgtgcagt tttgaatcat ttcccttatg ggacatttct gaaaaatgct  2340
ccccgttcgc ttgtagcact atgagagggg ccgaagactg caatggaggt agcgctgcgt  2400
tgaaaagacg aggcgctaca tttcgcgtag cgacaaggcc gtgtagagtt ttgcttttcg  2460
cgagacactg ctctgagtgt catatgcatc aaatgcagtg gtagcacaca gaggtgagaa  2520
gaatgatcac ctgcggggga atggctttgc taaacaacaa ggtcgctgtg tgactttaca  2580
caacgaaact actgtggtga gtgctcagtt gagtgaaaag aaatgccgcg ttatcgtgag  2640
ttctggttcg gtggactttg ccaccgtagt aaaactcaac ctgtaacgga atgcccagtt  2700
ttactgctct ctttaaaggg cgtccacgtt ctctatattc aagctgttta cccacctgcg  2760
tttcggtgca tcgcgcgtgc cacatcaaaa atccaggtaa cggtgcggga cctatgctac  2820
actttatatc tctcagaaag catacaccca ctgattatgg acaacgctgt ggtcgcgttg  2880
taccacaatg caggaatact cagttcacct tgcaagtgtt ctggtgttca ttgcgtgtca  2940
gaagtacacg aaaagagact tctttggcct ccaagtgata cgtaaccgcg gcagtcatga  3000
acagagtcac tcgtgcttct gaaacgcacg tcttctgtac agagacagat gcagtgtgca  3060
tacaggaagc ccctcgattg ttgccgtagc aggtagccag tagaagaaac aaagacacgg  3120
t                                                                 3121
```